US011123467B2

(12) United States Patent
Josephs et al.

(10) Patent No.: US 11,123,467 B2
(45) Date of Patent: Sep. 21, 2021

(54) SYSTEM AND METHOD FOR REMOVAL OF IMMUNE INHIBITORS FROM BIOLOGICAL FLUIDS

(71) Applicant: Immunicom, Inc., San Diego, CA (US)

(72) Inventors: Steven Josephs, San Diego, CA (US); Matthew Ong, San Diego, CA (US); Amir Jafri, San Diego, CA (US); Robert Segal, San Diego, CA (US); Stephen Prince, San Diego, CA (US)

(73) Assignee: IMMUNICOM, INC., San Diego, CA (US)

( * ) Notice: Subject to any disclaimer, the term of this patent is extended or adjusted under 35 U.S.C. 154(b) by 0 days.

(21) Appl. No.: 17/060,984

(22) Filed: Oct. 1, 2020

(65) Prior Publication Data

US 2021/0146030 A1 May 20, 2021

Related U.S. Application Data

(63) Continuation of application No. 16/688,409, filed on Nov. 19, 2019.

(51) Int. Cl.
*A61M 1/36* (2006.01)
*G01N 33/543* (2006.01)
(Continued)

(52) U.S. Cl.
CPC .......... *A61M 1/362* (2014.02); *A61M 1/3496* (2013.01); *A61M 1/36* (2013.01);
(Continued)

(58) Field of Classification Search
CPC ....... G01N 33/54313; G01N 33/54366; G01N 33/6863; G01N 2333/70578; A61M 1/362; C07K 14/525
See application file for complete search history.

(56) References Cited

U.S. PATENT DOCUMENTS

2007/0083145 A1 4/2007 Murakami et al.
2013/0264288 A1* 10/2013 Hlavinka ............ A61M 1/0218 210/650

(Continued)

FOREIGN PATENT DOCUMENTS

| | | | |
|---|---|---|---|
| EP | 0810027 | A1 | 12/1997 |
| EP | 1243298 | A1 | 9/2002 |
| WO | 2018/020285 | A2 | 2/2018 |

OTHER PUBLICATIONS

Xanthoulea et al. Tumor Necrosis Factor (TNF) Receptor Shedding Controls Thresholds of Innate Immune Activation That Balance Opposing TNF Functions in Infectious and Inflammatory Diseases. J. Exp. Med. 200 (3): 367-376 (Aug. 2, 2014).*

(Continued)

*Primary Examiner* — Gailene Gabel

(74) *Attorney, Agent, or Firm* — Pillsbury Winthrop Shaw Pittman LLP

(57) ABSTRACT

The present system and method are useful for the removal of immune inhibitors such as soluble TNF receptors from the body fluid of cancer patients. In some embodiments, soluble TNF-Receptors 1 and 2 are selectively removed from plasma at 80% or more efficiency. In some embodiments, the system includes an immobilized capture ligand of a single chain TNFα. The system and method are useful for the treatment of different cancer types, stages and severity.

14 Claims, 11 Drawing Sheets

Specification includes a Sequence Listing.

(51) Int. Cl.

| | |
|---|---|
| ***C07K 14/525*** | (2006.01) |
| ***G01N 33/68*** | (2006.01) |
| ***A61M 1/34*** | (2006.01) |

(52) U.S. Cl.

CPC ..... *C07K 14/525* (2013.01); *G01N 33/54313* (2013.01); *G01N 33/54366* (2013.01); *G01N 33/6863* (2013.01); *A61M 2202/0415* (2013.01); *G01N 2333/70578* (2013.01)

(56) References Cited

U.S. PATENT DOCUMENTS

| | | | | |
|---|---|---|---|---|
| 2014/0074007 | A1* | 3/2014 | McNeil | B01J 20/3212 604/4.01 |
| 2014/0303542 | A1 | 10/2014 | Leberthon | |
| 2015/0093289 | A1 | 4/2015 | Tullis | |
| 2017/0173231 | A1 | 6/2017 | Kiriyama et al. | |
| 2019/0247560 | A1 | 8/2019 | Storr et al. | |
| 2019/0262528 | A1 | 8/2019 | Mandry | |
| 2020/0171084 | A1* | 6/2020 | Joyce | C07K 14/42 |

OTHER PUBLICATIONS

Patent Cooperation Treaty, International Search Report issued in PCT/US2019/062177, dated Aug. 18, 2020, pp. 1-4.

European Patent Office, Supplementary European Search Report issued in EP Application No. 19920634, Mar. 24, 2021, pp. 1-4.

Taiwan Intellectual Property Office, Office Action Search Report issued in TW Patent Application No. 108142585, dated Aug. 5, 2021, p. 1.

* cited by examiner

SYSTEM AND METHOD FOR REMOVAL OF IMMUNE INHIBITORS FROM BIOLOGICAL FLUIDS

RELATED PATENT APPLICATIONS

This patent application is a continuation filing of, and claims the benefit of, U.S. patent application Ser. No. 16/688,409, filed on Nov. 19, 2019, the contents of which are hereby incorporated by reference in their entirety.

SEQUENCE LISTING

The present application is being filed with a Sequence Listing. The Sequence Listing is submitted electronically in ASCII format via EFS-Web in the form of a text file. Said ASCII copy, created on Oct. 1, 2020, is named "IMMUNICOM-0515378_ST25.txt" and is 10.3 KB in size, the contents of which are incorporated herein by reference in their entirety.

1. FIELD

The present disclosure pertains to a system and method for removal of immune inhibitors from plasma.

2. INTRODUCTION

Leveraging of the immune system to kill cancer has been the focus of oncologists and cancer researchers for more than a century. Observations that patient tumors enter remission subsequent to immune stimulating bacterial infections (see, for example, Coley, W. B. (1991). Clin Orthop Relat Res, 3-11; Hughes, W. T., and Smith, D. R. (1973) Cancer 31, 1008-1014; Yates, J. W., and Holland, J. F. (1973) Cancer 32, 1490-1498; Muller, H. E. (1974) (author's translation), Pathol Microbiol (Basel) 40, 297-304) as well as correlations between immune cell infiltration of cancer and survival (see, for example, Lipponen, P. K., et al. (1992) Eur J Cancer 29A, 69-75; Ma, D., and Gu, M. J. (1991) J Tongji Med Univ 11, 235-239; Pastrnak, A., and Jansa, P. (1989) Acta Univ Palacki Olomuc Fac Med 124, 7-71; Di Giorgio, et al. (1992) Int Surg 77, 256-260); Di Giorgio, A., et al. (1992) Int Surg 77, 256-260), have suggested the possibility of immunological control of neoplasia. It was however, only in the last decade that workers in the field of cancer immunotherapy have been able to claim significant improvements in patients' prognosis. A major accomplishment in the field was the development of antibodies that suppress the negative regulators or checkpoints of T-cell activation. These antibodies belong to a class of drugs termed "immune checkpoint inhibitors". The first one cleared by the FDA, Ipilimumab, an antagonistic antibody targeting cytotoxic T-lymphocyte-associated protein 4 (CTLA-4), improved overall survival in metastatic melanoma patients in 2010. An associated study assessed a total of 676 HLA-A*0201-positive patients with unresectable stage III or IV melanoma which were assigned to receive Ipilimumab plus glycoprotein 100 (gp100; also known as melanocyte protein) (403 patients), Ipilimumab alone (137), or gp100 alone (136). The median overall survival was 10.0 months among patients receiving Ipilimumab plus gp100, as compared with 6.4 months among patients receiving gp100 alone (hazard ratio for death, 0.68; P<0.001). The median overall survival with Ipilimumab alone was 10.1 months (hazard ratio for death in the comparison with gp100 alone, 0.66; P=0.003). No difference in overall survival was detected between the Ipilimumab groups (hazard ratio with Ipilimumab plus gp100, 1.04; P=0.76) (see, for example, Hodi, F. S., et al. (2010) N Engl J Med 363, 711-723). Following the success of anti-CTLA-4 therapy, antibodies targeting programmed cell death protein 1 (PD-1), or its ligand PD-L1, proved to be effective at improving overall survival in a wide variety of cancers (see, for example, Hamid, O., et al. (2013) N Engl J Med 369, 134-144; Herbst, R. S., et al. (2014) Nature 515, 563-567; Powles, T., et al. (2014) Nature 515, 558-562; Topalian, S. L., et al. (2014) J Clin Oncol 32, 1020-1030; Ribas, A., and Wolchok, J. D. (2018) Science 359, 1350-1355). For example, in one study, 296 patients received anti-PD-1 ligand antibody treatment. Among 236 patients in whom a response could be evaluated, objective responses (complete or partial responses) were observed in those with non-small-cell lung cancer, melanoma, or renal-cell cancer. Cumulative response rates (all doses) were 18% among patients with non-small-cell lung cancer (14 of 76 patients), 28% among patients with melanoma (26 of 94 patients), and 27% among patients with renal-cell cancer (9 of 33 patients). Responses were durable; 20 of 31 responses lasted 1 year or more in patients with 1 year or more of follow-up (see, Topalian, S. L., et al. (2012) N Engl J Med 366, 2443-2454). The encouraging results of these studies has sparked an interest from the cancer research field and inspired further investigations into targeting of alternative immune checkpoint molecules.

While checkpoint blockade represents a breakthrough in cancer therapy, a majority of cancer patients do not respond to these treatments, and some tumor types appear to be intrinsically resistant. The treatment is designed to boost an ongoing immune response and is inefficient in cases where initial immune activation is lacking, including tumors that are devoid of infiltrating T-cells. Development of therapeutic strategies to enhance immune cell recruitment may therefore increase the proportion of patients responding to immune checkpoint blockade. Limitations of checkpoint inhibitors include systemic exposure of the patient to the antibodies used, as well as inability to consistently induce responses.

TNFα (Tumor Necrosis Factor-alpha or herein interchangeably referred to as TNF) promotes anti-cancer activity and as its name implies, is a potent cytokine initially characterized as an anti-tumor agent (see, for example, Carswell, E. A., et al. (1975) Proc Natl Acad Sci USA 72, 3666-3670). Subsequently, TNF was shown to have both pro-tumor and anti-tumor effects depending on its contextual activity within the tumor microenvironment (see, for example, Wang, X., and Lin, Y. (2008) Acta Pharmacol Sin 29, 1275-1288). In the tumor microenvironment, expression of TNF at low levels contributes to angiogenesis, vessel permeability, and metastatic potential; whereas at high levels and during therapeutic delivery to tumors, TNF has shown anti-tumor effects including disruption of vascular integrity through apoptosis, direct tumor killing, and induction of anti-tumor immune responses (see, for example, Berberoglu, U., et al. (2004) Int J Biol Markers 19, 130-134; Michalaki, V., et al. (2004) Br J Cancer 90, 2312-2316; Talmadge, J. E., et al. (1987) Cancer Res 47, 2563-2570). Beneficial effects of elevated TNF in the clinical setting have been reported. For example, a study of TNF expression in 61 non-small cell lung carcinoma patients demonstrated expression of TNF in 45.9% of cases that directly correlated with a more favorable clinical outcome (see, for example, Boldrini, L., et al., G. (2000) Br J Cancer 83, 480-486). TNF administration is approved for isolated limb administration and has shown clinical benefit in isolated hepatic procedures for liver cancer.

sTNF-Rs (soluble receptors of TNF) inhibit anti-cancer immune responses and contribute to the control of TNF toxicity. The natural control or attenuation of TNF anti-tumor effects are attributed to the presence of inhibitory molecules comprising shed soluble TNF receptors that are present in the plasma and bind/neutralize TNF (see, for example, Xanthoulea, S., et al. (2004) J Exp Med 200, 367-376; Aderka, D., et al. (1998) J Clin Invest 101, 650-659; Aderka, D., et al. (1991) Cancer Res 51, 5602-5607; Selinsky, C. L., et al. (1998) Immunology 94, 88-93; Selinsky, C. L., and Howell, M. D. (2000) Cell Immunol 200, 81-87). The cancer promoting activities of these soluble inhibitors was discovered after initial observations of cancer regressions that occurred in patients undergoing plasmapheresis (see, for example, Israel, L., et al. (1976) Lancet 2, 642-643; Israel, L., et al. (1977) Cancer 40, 3146-3154). Subsequent studies showed that this observation was attributed to the removal sTNF-Rs. The molecular cloning of the cDNA and studies of the recombinant proteins confirmed their anti-TNF activity and pro-tumor function (see, for example, Schall, T. J., et al. (1990) Cell 61, 361-370; Engelmann, H., et al. (1990) J Biol Chem 265, 1531-1536).

At low doses of TNF, the normal concentrations of sTNF-R inhibitors can bind and inactivate the small amounts of administered TNF. However, dosing of increased amounts or the stimulation of higher TNF production to higher than normal levels can induce sTNF-R shedding that counteracts the ability of TNF to reach therapeutic anti-tumor concentrations without toxic effects. Thus, the ability to overcome TNF inhibition to achieve anti-cancer effects requires administration of TNF in amounts that are much too close to the maximum tolerated dose (MTD). For this reason, systemic TNF therapy, although possibly effective, has shown toxicity in numerous human clinical trials. Due to this adverse risk/benefit consideration, systemic therapy using TNF has largely been abandoned. However, isolated limb procedures that block systemic exposure to TNF have been performed in combination with chemotherapeutic agents (see, for example, Deroose, J. P., et al. (2012) Ann Surg Oncol 19, 627-635; Verhoef, C., et al. (2007) Curr Treat Options Oncol 8, 417-427).

There have been attempts to use medical devices which extracorporeally remove tumor produced immune "blocking factors." Unfortunately, to date, these devices have suffered many limitations such as: a) non-specific binding of other biological materials; b) "leaching" of immunoadsorptive materials from the device into patients' circulation; and c) ineffective removal of the target protein from circulation. The present invention overcomes these and other limitations of prior systems.

SUMMARY

The following is a non-exhaustive listing of some aspects of the present techniques. These and other aspects are described in the following disclosure.

Accordingly, one or more aspects of the present disclosure relate to a system for removing at least one target component of body fluid. The system comprises: an inlet configured to receive the body fluid from a patient and a sequestering chamber coupled to the inlet and configured to receive the body fluid from the inlet. The sequestering chamber comprises a capture support configured to bind to the at least one target component of the body fluid to capture the at least one target component in the sequestering chamber responsive to contact between the capture support and the body fluid. The capture support is configured to bind to the at least one target component to reduce an amount of the at least one target component in the body fluid. The sequestering chamber comprises first and second access ports configured to provide access to the sequestering chamber separate from the inlet. The first and second access ports are configured to facilitate insertion and/or removal of the capture support to and/or from the sequestering chamber. The system comprises an outlet configured to pass the body fluid having the reduced amount of the at least one target component from the sequestering chamber for optional reintroduction of some or all of the body fluid having the reduced amount of the at least one target component back into the patient; and one or more filters configured to separate the capture support in the sequestering chamber from the inlet and the outlet. The one or more filters are configured to retain the capture support within the sequestering chamber.

In an embodiment, (a) a capture efficiency of the capture support binding to the at least one target component is 80% or more at a flow rate of 45 mL per minute of plasma flow or less, and optionally (b) a binding affinity of the capture support to the at least one target component is at least about $10^{-7}$ $K_D$ and/or (c) a leach rate of the capture support through the outlet is less than about 100 ng/mL/min.

In an embodiment, (b) a binding affinity of the capture support to the at least one target component is $10^{-7}$ $K_D$ or greater, and optionally (a) a capture efficiency of the capture support binding to the at least one target component is 80% or more at a flow rate of 45 mL/min or less, and/or (c) a leach rate of the capture support through the outlet is less than about 100 ng/mL/min.

In an embodiment, (c) a leach rate of the capture support through the outlet is less than about 100 ng/mL/min, and optionally (a) a capture efficiency of the capture support binding to the at least one target component is 80% or more at a flow rate of 45 mL/min or less, and/or (b) a binding affinity of the capture support to the at least one target component is $10^{-7}$ $K_D$ or greater.

In an embodiment, the body fluid comprises plasma.

In an embodiment, the at least one target component comprises a protein, complex, assembly, or cell.

In an embodiment, the at least one target component comprises one or more plasma components that function to inhibit anti-cancer immune responses in the patient.

In an embodiment, the at least one target component comprises one or more immune inhibitors.

In an embodiment, the at least one target component comprises a soluble TNF-α receptor.

In an embodiment, the at least one target component comprises an sTNF-R1 receptor and/or an sTNF-R2 receptor.

In an embodiment, the capture support comprises an affinity chromatography support material. In other embodiments, the capture support comprises hollow fiber membranes, sheet or rolled sheet membranes, membrane cassettes, and/or beads.

In an embodiment, the capture support comprises the affinity chromatography support material, and the affinity chromatography support material comprises sepharose, agarose, or acrylamide.

In an embodiment, the capture support comprises a porous or non-porous matrix material including, but not limited to, ceramic material.

In an embodiment, the capture support is configured to bind to more than one target component of the body fluid.

In an embodiment, the capture support comprises a solid support having antibodies, antibody fragments, binding peptides, aptamers, or avimers immobilized thereon.

In an embodiment, the antibodies are selected from the group consisting of IgA, IgD, IgE, IgG, IgM, and combinations thereof.

In an embodiment, the capture support comprises TNFα, multimers of TNFα, single chain TNFα, fragments of TNFα, multimers of fragments of TNFα, or combinations thereof.

In an embodiment, multimers of TNFα comprise TNFα monomers in which one or more monomers is in an amino terminal to carboxyl terminal linkage.

In certain embodiments, multimers of TNFα can exclude or include a spacer between the monomers.

In certain embodiments, a spacer comprises one or more amino acid residues.

In an embodiment a spacer comprises one or more glycine, serine and/or alanine amino acids.

In an embodiment, the capture support comprises an sc-TNFα ligand, optionally the entire sequence or partial sequence of SEQ ID NO:1, SEQ ID NO:2, or SEQ: ID NO:3.

In an embodiment, the capture support comprises a trimeric form of the TNFα ligand.

In an embodiment, the trimeric form of the scTNFα ligand comprises the sequence of SEQ ID NO:2 or SEQ: ID NO:3, with or without the spacer amino acids.

In an embodiment, the capture support comprises ligands bound to beads.

In an embodiment, the ligands have a given density and orientation on a given bead. The density and/or orientation is configured to enhance binding between the ligands and the at least one target component of the body fluid.

In an embodiment, a size, number, density, and/or concentration of the beads is configured to facilitate a laminar flow of the body fluid through the beads to enhance the binding between the ligands and the at least one target component of the body fluid.

In an embodiment, the beads are quenched in ethanolamine to enhance binding specificity.

In an embodiment, the body fluid is whole blood.

In an embodiment, the inlet, the sequestering chamber, and the outlet form an extracorporeal closed-circuit column.

In an embodiment, the extracorporeal closed-circuit column is configured to remain sterile during operation.

In an embodiment, the system comprises a target component outlet port configured to facilitate sampling or removal of all or part of the captured at least one target component without compromising the extracorporeal closed-circuit column.

In an embodiment, the system comprises an elution reagent port configured to facilitate introduction of an elution reagent into the sequestering chamber without compromising the extracorporeal closed-circuit column.

In an embodiment, the elution reagent port is further configured to receive a conditioning agent configured to prepare the system for reuse.

In an embodiment, the system further comprises a pump configured to drive a reconditioning agent through the inlet, the sequestering chamber, and the outlet.

In an embodiment, the pump comprises a syringe pump, a peristaltic pump, a piston pump, a diaphragm pump, or a combination thereof.

In an embodiment, the one or more filters have an average pore diameter between about 3 microns and about 100 microns.

In an embodiment, the system further comprises one or more additional sequestering chambers including capture supports having the same functionality.

In an embodiment, the one or more additional sequestering chambers combine with the sequestering chamber to form a multistage separation circuit configured to bind with a plurality of different target components.

In an embodiment, the patient is a human or veterinary subject. The veterinary subject may include domestic animals such as dogs, cats, etc.; farm or ranch animals such as equine, porcine, bovine, etc.; and/or other animals.

According to another embodiment, a method for removing the at least one target component of the body fluid with the system of any of the embodiments described above is provided. The method comprises: conducting the body fluid from the patient through the inlet to the sequestering chamber; binding the at least one target component of the body fluid to capture the at least one target component in the sequestering chamber to reduce the amount of the at least one target component in the body fluid; and optionally passing some or all of the body fluid having the reduced amount of the at least one target component from the sequestering chamber through the outlet for reintroduction back into the patient.

In an embodiment, the method further comprises measuring the reduced amount of the at least one target component in the body fluid reintroduced back into the patient.

In an embodiment, the measuring comprises one or more of liquid chromatography—mass spectrometry (LC-MS), high performance liquid chromatography (HPLC), ultra-high performance liquid chromatography (UHPLC), resistance measurements, light emission measurements, chemiluminescence, electroluminescence, electrochemiluminescence, chromatographic monitoring, positron emission tomography (PET), x-ray computed tomography (CT), magnetic resonance imaging (MRI), ultrasound, gamma camera, single photon emission computed tomography (SPECT), ELISA, surface plasmon resonance (SPR) and/or biolayer interferometry (BLI).

In an embodiment, the method further comprises measuring a leach rate of the capture support in the body fluid reintroduced back into the patient.

In some embodiments, the method is for human, veterinary, domestic/companion animal, ranch/farm animal, and/or other use.

These and other objects, features, and characteristics of the system or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
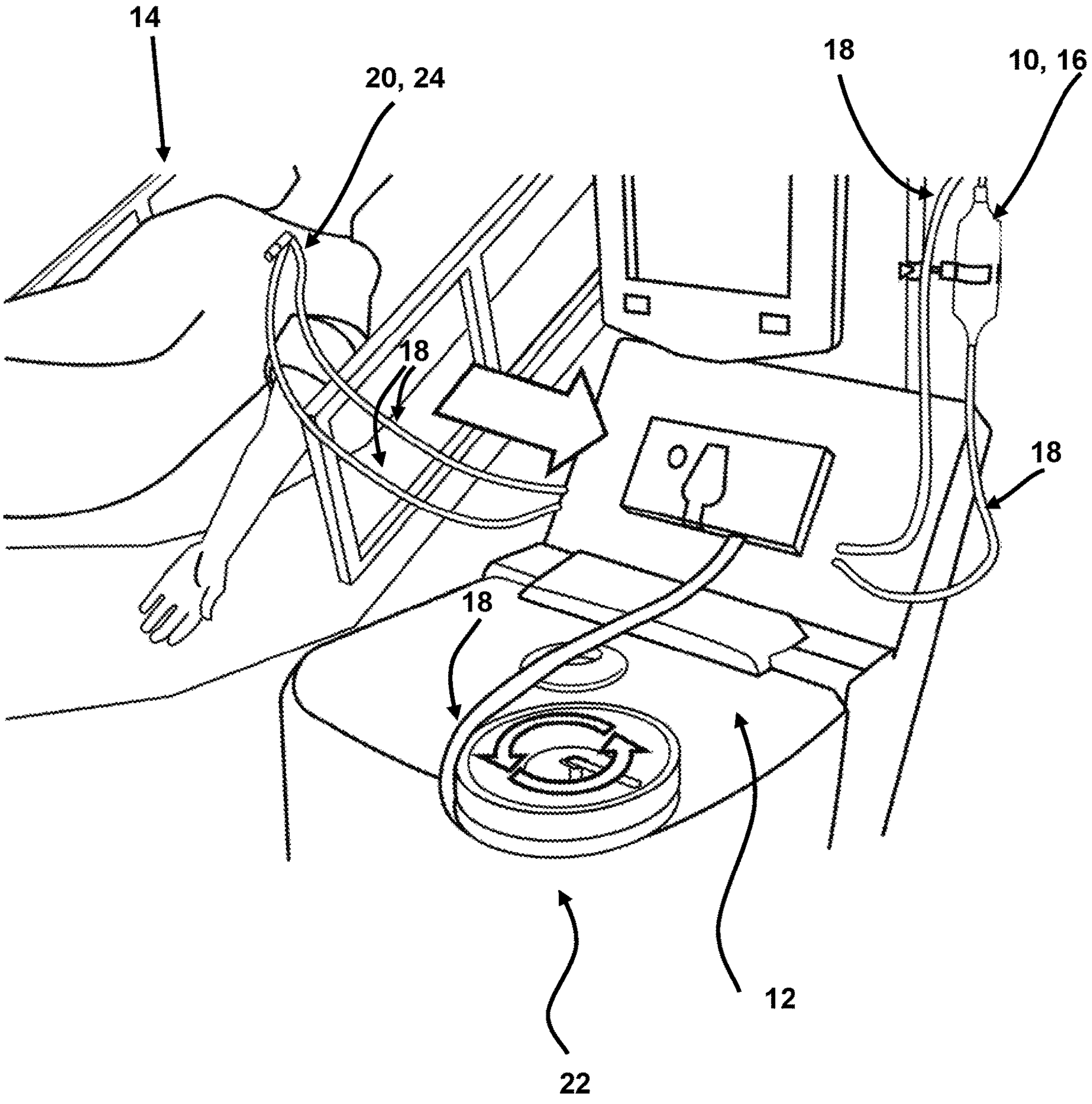
FIG. 1 illustrates an example embodiment of the present system, in accordance with one or more embodiments.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF EXEMPLARY EMBODIMENTS

To mitigate the problems described herein, the inventors had to both invent solutions and, in some cases just as importantly, recognize problems overlooked (or not yet foreseen) by others in the field. Indeed, the inventors wish to emphasize the difficulty of recognizing those problems that are nascent and will become much more apparent in the future should industry trends continue as the inventors expect. Further, because multiple problems are addressed, many of them simultaneously, it should be understood that some embodiments are problem-specific, and not all embodiments address every problem with traditional systems described herein or provide every benefit described herein. That said, improvements that solve various permutations of these problems are described below.

The present system and method are useful for immune modulation of cancer patients and may provide comparatively useful immune modulation for other diseases, including but not limited to, auto-immune and inflammatory disorders. In some embodiments, extracorporeal removal of immune suppressive factors from blood of patients using immunoadsorptive means is provided. In some embodiments, the present system and method provide for the efficient removal of soluble tumor necrosis factor receptors (sTNF-Rs) from cancer patients. TNF is an endogenous cytokine that modulates tumor growth and suppression as part of the body's natural immune response to cancer. However, in many cancers, the anti-tumor effects of TNF are blocked by the presence of circulating inhibitory molecules known as soluble TNF receptors (sTNF-R1 and sTNF-R2; see, for example, Gatanaga, T., et al. (1990) Lymphokine Res 9, 225-229; Gatanaga, T., et al. (1990) Proc Natl Acad Sci USA 87, 8781-8784; Schall, T. J., et al. (1990) Cell 61, 361-370; Berberoglu, U. et al. (2004) Int J Biol Markers 19, 130-134). These receptors, which block the therapeutic anti-tumor effects of endogenous TNF, have been shown to increase in cancers and correlate with disease stage (see, for example, Aderka, D., et al. (1991) Cancer Res 51, 5602-5607). sTNF-Rs are also a prognostic indicator for breast, malignant melanoma, colorectal, and bone sarcomas, and correlate negatively with patient survival (see, for example, Langkopf, F., and Atzpodien, J. (1994) Lancet 344, 57-58; Viac, J., et al. (1996) Eur J Cancer 32A, 447-449). Selective removal of sTNF-Rs from the patient's blood via plasma apheresis, a process known as Immunopheresis™ enhances the patient's natural anti-tumor immune response by unmasking the anti-tumor effects of endogenous TNF, which can facilitate reduction of tumor burden and improve patient survival.

FIG. 1 illustrates an example embodiment of the present system, (item 10). In FIG. 1, system 10 is shown coupled to an apheresis machine 12. System 10 is configured to selectively remove sTNF-Rs (e.g., soluble Tumor Necrosis Factor Receptor 1 (sTNF-R1), also known as tumor necrosis factor receptor superfamily member 1A (TNFRSF1A and CD120a); and soluble Tumor Necrosis Factor Receptor 2 (sTNF-R2), also known as tumor necrosis factor receptor superfamily member 1B (TNFRSF1B and CD120b), as example target components, from the blood of a cancer patient 14. System 10 includes a highly-selective binding matrix within a housing 16 that has various ports that facilitate filling and plasma flow during use. Blood drawn from patient 14 may be processed to obtain plasma, and the plasma treated by placing system 10 into a plasma flow line 18 of apheresis machine 12 for a plasmapheresis procedure.

Examples of commercially available apheresis machines 12 include a Terumo BCT Spectra Optia System, for example. Other manufacturers of apheresis machines include, but are not limited to, Fresenius, Haemonetics, Baxter, Nigale and Asahi. Apheresis may then be performed in accordance with the manufacturer's instructions.

As shown in FIG. 1, apheresis machine 12 may facilitate intravenous removal of blood 20 from patient 14 and then separation 22 of the blood into plasma and cell fractions (e.g., using centrifugal forces, a membrane filter, and/or other components). The plasma fraction is then pumped into system 10 where the plasma passes through a capture support (that includes a binding matrix as described herein) that captures, for example, sTNF-Rs using a TNF ligand (as described herein). The plasma is then pumped back out of system 10, where some or all of the treated plasma may be recombined with the separated cells of patient 14, and then reintroduced 24 back into the circulatory system of patient 14.

In some embodiments, treated plasma may be discarded and replaced by fresh plasma. For example, the plasma exchange may be concurrent where the exchange plasma is further treated to remove inhibitors. Immunopheresis (e.g., as described herein) could be done following plasma exchange, for example.

It should be noted that although blood, plasma, sTNF-R's and TNF ligands are specifically mentioned throughout this application, the components and/or principles described herein may be applied for other body fluids, other target components of a body fluid, and/or other capturing or binding elements.

Figure 2:
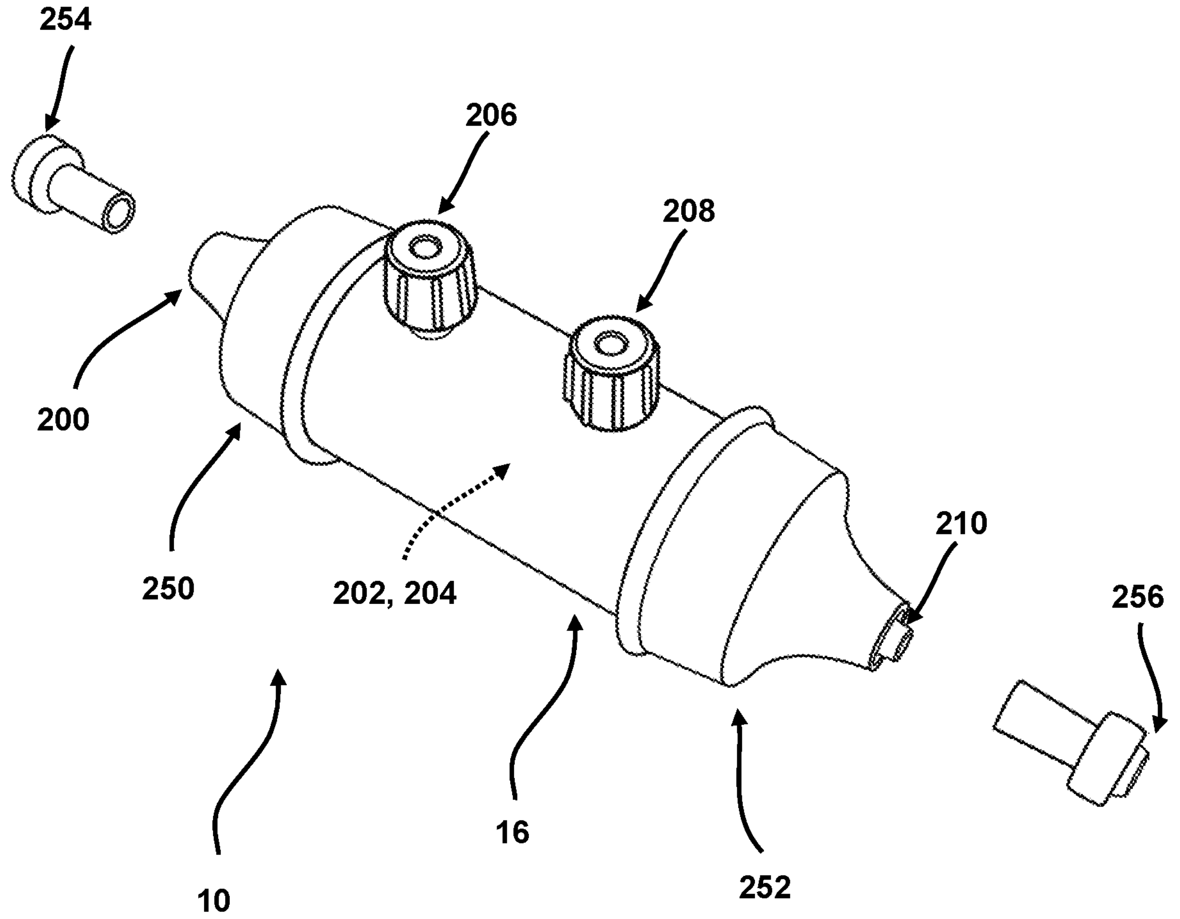
FIG. 2 provides a more detailed view of the present system, in accordance with one or more embodiments.
Figure 3:
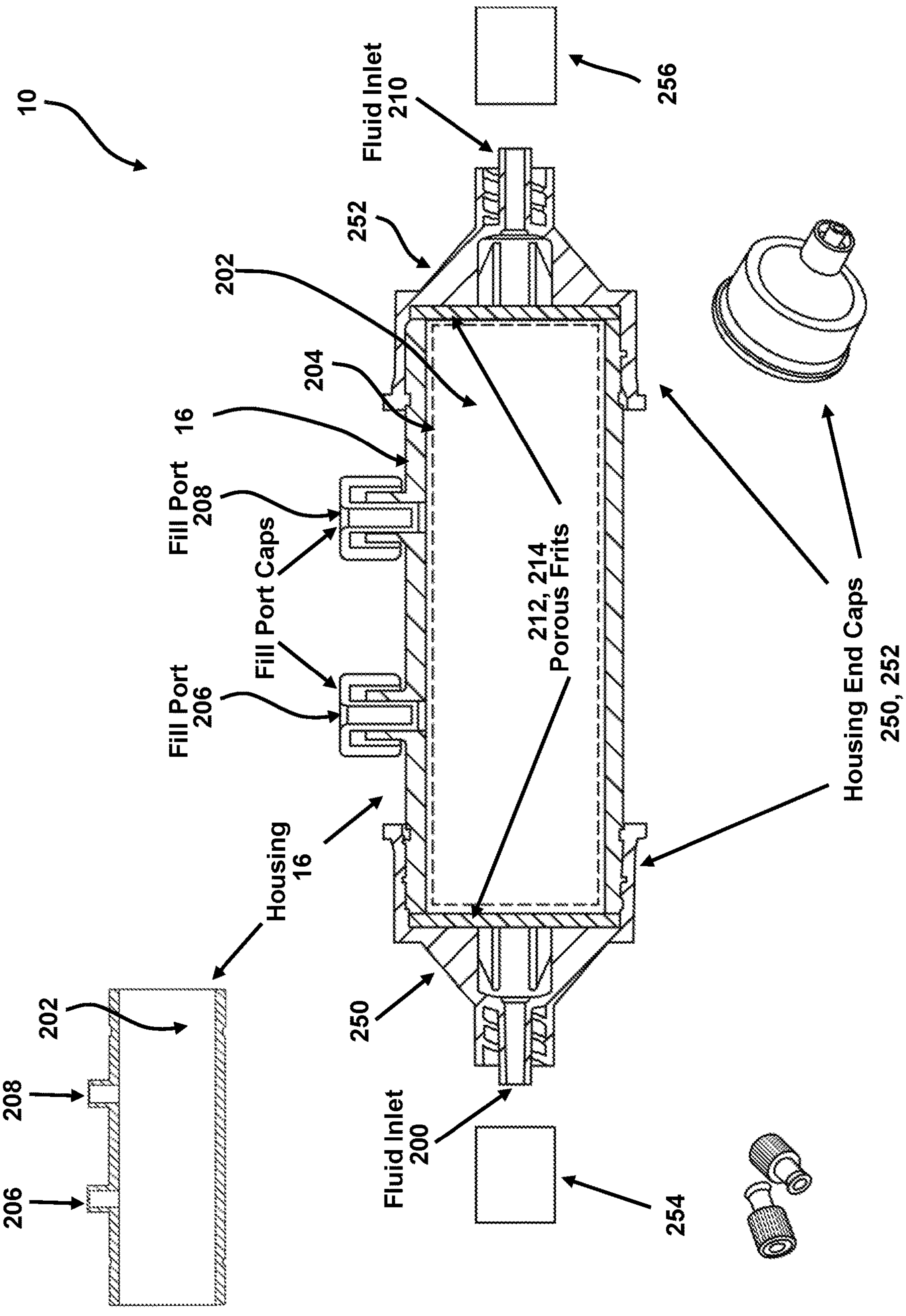
FIG. 3 illustrates a corresponding cross-sectional view of the present system, in accordance with one or more embodiments.

FIG. 2 provides a more detailed view of system 10. FIG. 3 illustrates a corresponding cross-sectional view. Referring to FIG. 2 and FIG. 3, system 10 comprises housing 16, an inlet 200, a sequestering chamber 202 that includes a capture support 204, access ports 206, 208, an outlet 210, one or more filters (e.g., 212 and 214 shown in FIG. 3), end caps 250 and 252, and/or other components. As shown in FIG. 2 and FIG. 3, system 10 may form an extracorporeal closed-circuit column, for example.

The closed-circuit column may be configured to remain sterile during operation. In some embodiments, the components of the system 10 are washed, for example, with 70% isopropyl alcohol prior to assembly to remove particulates. End caps 250 and 252 may be fitted with filters 212 and 214, and pressed onto the ends of a barrel or tube (for example) forming housing 16. Caps 254 and 256 may be screwed into and/or otherwise coupled with inlet 200 and outlet 210. This sub-assembly may be packaged and sterilized, for example, using ethylene oxide (EtO). EtO residuals may be allowed to dissipate prior to continuing production steps. The EtO sterilized subassembly may be aseptically filled with capture support 204 through access ports 206 and 208, and then ports 206 and 208 may be securely capped with polycarbonate (for example) Luer (for example) caps (e.g., as described herein). An assembled device may then be individually packaged and terminally sterilized using E-beam irradiation using 17.5-30 kGy (for example). In some embodiments, other means of sterilization that may be utilized include gamma irradiation, ethylene oxide, hydrogen peroxide, bleach, heat sterilization, steam sterilization, ozone and/or other sterilization operations depending on the stability of capture support 204 and/or other factors.

Housing 16, inlet 200, outlet 210, and/or other components of system 10 may be configured to couple with a (e.g., plasma) flow line of an apheresis machine (e.g., machine 12 as shown in FIG. 1). Housing 16, inlet 200, outlet 210, and/or other components of system 10 may be configured to couple with the flow line of the apheresis machine at a point in the flow line that is after the patient's blood has been separated (e.g., as described herein) into cellular and plasma fractions, for example. Housing 16 may form a fluid channel or flow path to conduct the body fluid of a patient between inlet 200 and outlet 210.

Housing 16 may provide structural support for capture support 204 and/or other components of system 10. Housing 16 may form an elongated tubular body having a circular cross-sectional shape, and/or other cross-sectional shapes. Housing 16 may house sequestering chamber 202 including capture support 204, one or more filters 212 and/or 214, and/or other components. In some embodiments, housing 16 and/or other components of system 10 may be manufactured by injection molding and/or other operations.

Housing 16 may house filters 212 and 214 such that filters 212 and 214 are substantially perpendicular to a fluid flow direction between inlet 200 and outlet 210. Filters 212 and 214 may be configured to separate capture support 204 in the sequestering chamber 202 from inlet 200 and outlet 210. Filters 212, 214 may be configured to retain capture support 204 within sequestering chamber 202, and/or perform other functions.

In some embodiments, filters 212 and/or 214 may form porous barriers mounted substantially perpendicular to a direction of fluid flow through housing 16. Filter 212 may be located proximate to inlet 200, and filter 214 may be located proximate to outlet 210, thereby forming sequestering chamber 202 inside housing 16. Filters 212 and/or 214 may be configured to prevent portions (up to and including all) of capture support 204 (e.g., one or more beads as described herein) from escaping system 10 and passing into a patient's circulatory system, for example. In some embodiments, filters 212 and/or 214 may comprise porous frits, for example. In some embodiments, filters 212, 214 may have an average pore diameter between about 3 microns and about 100 microns, for example, and/or other average pore diameters. In some embodiments, filters 212 and 214 may have a diameter that is larger than an inner diameter of housing 16 such that filters 212 and 214 fit snugly within housing 16 and do not move when body fluid flows through system 10. In some embodiments, filters 212 and 214 are held in place by pressure from end caps 250 and 252 (described below) pressing filters 212 and 214 against rims of housing 16 (e.g., at either end of a tube formed by housing 16). In some embodiments, filters 212 and 214 are held in place within housing 16 by other mechanisms such as adhesives, washers, gaskets, stitching, over-molding, ultrasonic welding, and/or other components and/or processes. In some embodiments, filters 212 and 214 may be formed from polyethylene and/or other materials.

In some embodiments, housing 16 includes end caps 250 and 252 at either end of housing 16 that form and/or include inlet 200 and outlet 210. End caps 250 and 252 may be threaded to housing 16 and/or be coupled to housing 16 in other ways (e.g., via clips, clamps, adhesive, ultrasonic welding, pressure fitted, etc.). In some embodiments, end caps 250 and/or 252 may be affixed onto housing 16 to ensure system 10 is substantially airtight. In other words, system 10 is configured to withstand internal and external pressure forces (both air and fluid) to ensure sterility during storage, shipping, and use. In some embodiments, end caps 250 and 252 terminate at inlet 200 and outlet 210, respectively. In some embodiments, inlet 200 and/or outlet 210 may include caps 254, 256. In some embodiments, end caps 250 and/or 252 may be formed from polypropylene and/or other materials. In some embodiments, caps 254 and/or 256 may be formed from high density polyethylene and/or other materials, for example.

In some embodiments, housing 16 may be formed from plastic and/or other materials. For example, housing 16 may be formed from one or more of ECTFE (ethylene-chlorotrifuluoroethylene copolymer, halar ECTFE, ETFE (ethylene-tetrafluoroethylene), tefzel ethylene tetrafluoroethylene (ETFE), FEP (fluorinated ethylene polypropylene), HDPE (high density polyethylene), LDPE (low density polyethylene), PC (polycarbonate), Makrolon polycarbonate, PEI (polytheterimide), PET (polyethylene terephthalate), PETG (polyethylene terephthalate copolymer), PFA (polyfluoroalkoxy), Teflon PFA, PMMA (polymethyl methacrylate), PMP (polymethypentene), polypropylene, PPCO (polypropylene copolymer), polystyrene, PSF (polysulfone), PTFE (polytetrafluoroethylene), SAN (styrene acrylonitrile), TFE (tetrafluoroethlene), Teflon TFE, TMX (thermanox), PMX (permanox), and/or other materials. In some embodiments, housing 16 may be formed from metallic materials (e.g., iron, iron alloy, steel, stainless steel, aluminum, aluminum alloy), glass and/or other materials.

Inlet 200 may be configured to receive blood, plasma, and/or other body fluids from a patient (e.g., patient 14 shown in FIG. 1). Outlet 210 may be configured to pass blood, plasma, and/or other body fluid having a reduced amount of one or more target components from sequestering chamber 202 for reintroduction back into the patient (e.g., patient 14 shown in FIG. 1). In some embodiments, inlet 200 and/or outlet 210 may be a Luer fitting and/or other inlet or outlet fluidic connector types or configurations. In some embodiments, inlet 200 and/or outlet 210 are configured to be fluidically coupled to apheresis machine tubing sets, intravenous tubing extension sets, fluidic tubing adapters, filters, stopcocks, and/or other elements commonly used in closed-loop patient fluid line assemblies. In some embodiments, inlet 200 and/or outlet 210 may be configured such that the blood, plasma, and/or other body fluids from a patient flow through system 10 at a flow rate of between about 5 mL/min and about 300 mL/min, and/or other flow rates. In some embodiments, the flow rate may be between about 10 mL/min and about 100 mL/min. In some embodiments, the flow rate may be between about 25 mL/min and about 75 mL/min. In some embodiments, the flow rate may be between about 35 mL/min and about 70 mL/min. In some embodiments, the flow rate may be between about 40 mL/min and about 60 mL/min. These exemplary flow rates are in the range that can be accommodated by the system described herein. For some procedures, flow rates of less than 5 mL/min may require an inordinate amount of time to complete. Conversely, flow rates of over 300 mL/min may limit capture efficiency of the system 10 when used in conjunction with an apheresis machine. However, it is anticipated that flow rates of 300 mL/min are possible. Inlet 200 and/or outlet 210 may have a diameter of a specific size and/or other features that facilitate such flow rates.

In some embodiments, inlet 200 and/or outlet 210 may be configured such that human plasma containing up to about 200 micrograms (for example) of sTNF-R proteins flow through system 10. This example is based on an expected total plasma amount of sTNF-Rs of the patient. The concentration range of sTNF-Rs (combined sTNF-R1 and sTNF-R2) in human plasma is approximately 3-10 ng/mL and the plasma volume of an example patient may be in the range of 50 cc per Kg body weight (W). The total amount of sTNF-R is about (W(Kg)×50 mL/Kg×(3-10 ng/mL)/1000 ng/μg). Thus, for an individual of 70 Kg (for example), the amount of sTNF-Rs would be in the range of 10.5 to 35 micrograms. In some embodiments, an excess amount of capture capability of system 10 may create an ample margin of efficiency based on laboratory bench testing of excessive amounts of sTNF-Rs with plasma flow through system 10 at rates of up to about 45 mL/min (for example). In some embodiments, inlet 200 and/or outlet 210 may be formed from polypropylene, polycarbonate, Makrolon™ and/or other materials.

Sequestering chamber 202 may be coupled to inlet 200. Sequestering chamber 202 may be configured to receive the blood (e.g., whole blood), plasma, and/or other body fluid from inlet 200. Sequestering chamber 202 may comprise capture support 204, access ports 206, 208, and/or other components.

Capture support 204 may be configured to bind to at least one target component of the blood, plasma, and/or other body fluid to capture the at least one target component in sequestering chamber 202. Capture support 204 may be and/or include a binding matrix (comprising beads ligands and/or other components as described herein), for example. The capturing may occur responsive to contact between capture support 204 and the blood, plasma, and/or other body fluid. Capture support 204 may be configured to bind to the at least one target component to reduce an amount of the at least one target component in the blood, plasma, and/or other body fluid.

In some embodiments, the at least one target component may comprise a complex, an assembly, or a cell. In some embodiments, the at least one target component may comprise one or more blood products such as plasma or serum components that function to inhibit anti-cancer immune responses in the patient. In some embodiments, the at least one target component may comprise one or more immune inhibitors. For example, the at least one target component may comprise a soluble TNFα receptor, an sTNF-R1 receptor, an sTNF-R2 receptor, an sTNF-R1 and sTNF-R2 receptor, and/or other receptors and receptor combinations.

In some embodiments, the capture moiety may be selected so as to bind to and capture other specific molecules in the plasma. Examples of these other molecules or targets are, but are not limited, to acetyl-choline receptors, adenosine receptors, adrenoreceptors, GABA receptors, angiotensin receptors, cannabinoid receptors, cholecystokinin receptors, dopamine receptors, glucagon receptors, glucocorticoid receptors, glutamate receptors, histamine receptors, mineralocorticoid receptors, olfactory receptors, opioid receptors, purinergic receptors, secretin receptors, serotonin receptors, somatostatin receptors, steroid hormone receptors, calcium-sensing receptors, hormone receptors, erythropoietin receptors, and natriuretic peptide receptors or their ligands. Other examples include but are not limited to type I cytokine receptors such as type I interleukin receptors, erythropoietin receptor, GM-CSF receptor, G-CSF receptor growth hormone receptor, oncostatin M receptor, myostatin receptor, leukemia inhibitory factor receptor; type II cytokine receptors such as type II interleukin receptors, interferon-α/β receptors, interferon-γ receptor or their ligands; members of the immunoglobulin superfamily such as interleukin-1 receptor, CSF1, ckit receptor, interleukin-18 receptor or their ligands; CD27, CD40 and lymphotoxin receptor or their ligands; chemokine receptors including serpentine CCR and CXCR receptors such as CCR1 and CXCR4, and interleukin 8 receptor or their ligands; TGF β receptors including TGF β receptor 1 and TGF β receptor 2 or their ligands; galectins; and/or other structures (see Ozaki and Leonard, J. Biol. Chem 277:29355-29353, 2002).

In some embodiments, capture support 204 may comprise a solid support and/or other components. The solid support may be an affinity chromatography support material, hollow fiber membranes, sheet membranes, membrane cassettes, rolled sheet membranes, and/or other materials. In embodiments where capture support 204 comprises the affinity chromatography support material, the affinity chromatography support material may comprise a sugar, carbohydrate or polysaccaharide such as sepharose, agarose, or a polymer such as acrylamide, and/or other materials.

In some embodiments, capture support 204 may comprise a porous or non-porous matrix material. In some embodiments, capture support 204 may be configured to bind to more than one target component of the blood, plasma, and/or other body fluid.

In some embodiments, capture support 204 may be an affinity chromatography matrix comprising different capture moieties including but not limited to affinity reagents (e.g., a ligand as described herein) bound to a support. The affinity chromatography matrix may alternatively comprise a linking group, such as, but not limited to, cyanogen bromide, tresyl, triazine, vinyl sulfone, an aldehyde, an epoxide, or an activated carboxylic acid to facilitate coupling of an affinity reagent (e.g., a ligand) to the solid support. The chromatography matrix may be prepared by coupling the methyl-lysine affinity reagent to the solid support with a linking group by chemically activating the solid support, if necessary, and contacting the solid support with the methyl-lysine affinity reagent such that the affinity reagent covalently attaches to the solid support. Additionally, the affinity reagent may be coupled to the solid support through a linker to make the affinity reagent more accessible for binding to methylated proteins and peptides.

In some embodiments, capture support 204 may comprise a solid support having antibodies, antibody fragments, binding peptides, aptamers, avimers, and/or other components immobilized thereon. In some embodiments, the antibodies are one or more of IgA, IgD, IgE, IgG, or IgM, immunoglobulin subclasses and mixtures thereof, combinations thereof, and/or other antibodies.

In some embodiments, capture support 204 may comprise an affinity reagent comprising ligands such as TNFα (as described above, TNF and TNFα are used interchangeably herein), multimers of TNF, single chain (sc) TNF, fragments of TNF, multimers of fragments of TNF, or combinations thereof. In some embodiments, capture support 204 may be and/or include TNF ligands bound to one or more solid supports. In some embodiments, the binding may be covalent linking and/or other binding, for example.

Types of TNF include mammalian TNF, such as primate TNF and human TNF. Exemplary human TNF sequences comprise:

```
(SSSRTPSDKPVAHVVANPQAEGQLQWLNRRANALLANGVEL

RDNQLVVPSEGLYLIYSQVLFKGQGCPSTHVLLTHTISRIAV

SYQTKVNLLSAIKSPCQRETPEGAEAKPWYEPIYLGGVFQLE

KGDRLSAEINRPDYLDFAESGQVYFGIIAL,
SEQ ID NO: 1)-[processed TNF monomer,
from Genbank Accession No. AQY77150.1];

Trimeric form:
(MCGSHHHHHHGSASSSSRTPSDKPVAHVVANPQAEGQLQWL

NRRANALLANGVELRDNQLVVPSEGLYLIYSQVLFKGQGCPS

THVLLTHTISRIAVSYQTKVNLLSAIKSPCQRETPEGAEAKP

WYEPIYLGGVFQLEKGDRLSAEINRPDYLDFAESGQVYFGII

ALGGGSGGGSGGGSGGGSSSRTPSDKPVAHVVANPQAEGQLQ

WLNRRANALLANGVELRDNQLVVPSEGLYLIYSQVLFKGQGC

PSTHVLLTHTISRIAVSYQTKVNLLSAIKSPCQRETPEGAEA

KPWYEPIYLGGVFQLEKGDRLSAEINRPDYLDFAESGQVYFG

IIALGGGSGGGSGGGSGGGSSSRTPSDKPVAHVVANPQAEGQ

LQWLNRRANALLANGVELRDNQLVVPSEGLYLIYSQVLFKGQ
```

-continued

```
GCPSTHVLLTHTISRIAVSYQTKVNLLSAIKSPCQRETPEGA

EAKPWYEPIYLGGVFQLEKGDRLSAEINRPDYLDFAESGQVY

FGIIAL,
SEQ ID NO: 2);
and

Trimeric form:
(G S A S S S S R T P S D K P V A H V V A N

P Q A E G Q L Q W L N R R A N A L L A N G

V E L R D N Q L V V P S E G L Y L I Y S Q

V L F K G Q G C P S T H V L L T H T I S R

I A V S Y Q T K V N L L S A I K S P C Q R

E T P E G A E A K P W Y E P I Y L G G V F

Q L E K G D R L S A E I N R P D Y L D F A

E S G Q V Y F G I I A L G G G S G G G S G

G G S G G G S S S R T P S D K P V A H V V

A N P Q A E G Q L Q W L N R R A N A L L A

N G V E L R D N Q L V V P S E G L Y L I Y

S Q V L F K G Q G C P S T H V L L T H T I

S R I A V S Y Q T K V N L L S A I K S P C

Q R E T P E G A E A K P W Y E P I Y L G G

V F Q L E K G D R L S A E I N R P D Y L D

F A E S G Q V Y F G I I A L G G G S G G G

S G G G S G G G S S S R T P S D K P V A H

V V A N P Q A E G Q L Q W L N R R A N A L

L A N G V E L R D N Q L V V P S E G L Y L

I Y S Q V L F K G Q G C P S T H V L L T H

T I S R I A V S Y Q T K V N L L S A I K S

P C Q R E T P E G A E A K P W Y E P I Y L

G G V F Q L E K G D R L S A E I N R P D Y

L D F A E S G Q V Y F G I I A L,
SEQ ID NO: 3).
```

Exemplary TNF can comprise a monomer of the sequence of SEQ ID NO:1, a dimer of the sequence of SEQ ID NO:1, a trimer of the sequence of SEQ ID NO:1 or the timeric form, SEQ ID NO:2 or SEQ ID NO:3, or a partial sequence thereof. The monomers comprising SEQ ID NO:2 or SEQ ID NO:3 may optionally be covalently linked by a spacer sequence of glycines or serines, such as GGGS, or spacer multimers such as $(GGGS)_4$. Amino acids, spacer sequences and spacer multimers may or may not be incorporated into dimeric or trimeric forms.

Naturally and non-naturally occurring variants of TNF are included. Such variants include gain and loss of function variants.

Non-limiting examples of TNF variants include one or more amino acid substitutions (e.g., 1-3, 3-5, 5-10, 10-15, 15-20, 20-25, 25-30, 30-40, 40-50, 50-100, or more residues), additions (e.g., insertions or 1-3, 3-5, 5-10, 10-15, 15-20, 20-25, 25-30, 30-40, 40-50, 50-100, or more residues) and deletions (e.g., subsequences or fragments) of a reference TNF sequence. In some embodiments, a variant TNF sequence retains at least part of a function or an activity of unmodified sequence, such as the ability to bind to sTNF-R's (e.g., sTNF-R1 receptor and/or sTNF-R2 receptor).

A variant can have one or more non-conservative or a conservative amino acid sequence differences or modifications, or both. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like. Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. For example, conservative amino acid substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. A "conservative substitution" also includes the use of a substituted amino acid in place of an unsubstituted parent amino acid.

Such variants include proteins or polypeptides which have been or may be modified using recombinant DNA technology such that the protein or polypeptide possesses altered or additional properties, for example. Variants can differ from a reference sequence, such as naturally occurring proteins or peptides.

At the amino acid sequence level, a naturally or non-naturally occurring variant protein will typically be at least about 70% identical, more typically about 80% identical, even more typically about 90% or more identity to the reference protein, although substantial regions of non-identity are permitted in non-conserved regions (e.g., less, than 70% identical, such as less than 60%, 50% or even 40%). In other embodiments, the sequences have at least 60%, 70%, 75% or more identity (e.g., 80%, 85% 90%, 95%, 96%, 97%, 98%, 99% or more identity) to a reference sequence. Procedures for the introduction of amino acid changes in a protein or polypeptide are known to the skilled artisan (see, e.g., Sambrook et al., *Molecular Cloning: A Laboratory Manual* (2007)).

The term "identity" and grammatical variations thereof, mean that two or more referenced entities are the same, when they are "aligned" sequences. Thus, by way of example, when two polypeptide sequences are identical, they have the same amino acid sequence, at least within the referenced region or portion. The identity can be over a defined area (region or domain) of the sequence. An "area" or "region" of identity refers to a portion of two or more referenced entities that are the same. Thus, where two protein sequences are identical over one or more sequence areas or regions they share identity within that region. An "aligned" sequence refers to multiple protein (amino acid) sequences, often containing corrections for missing amino acids (gaps) as compared to a reference sequence.

The identity can extend over the entire sequence length or a portion of the sequence. For example, the length of the sequence sharing the percent identity is 2, 3, 4, 5 or more contiguous amino acids or more, e.g., 6, 7, 8, 9, 10, 11, 12, 13, 14, 15, 16, 17, 18, 19, 20, etc. contiguous amino acids. In another nonlimiting example, the length of the sequence sharing identity is 20 or more contiguous amino acids or more, e.g., 21, 22, 23, 24, 25, 26, 27, 28, 29, 30, 31, 32, 33, 34, 35, etc. contiguous amino acids. In a further nonlimiting example, the length of the sequence sharing identity is 35 or more contiguous amino acids, e.g., 36, 37, 38, 39, 40, 41, 42, 43, 44, 45, 45, 47, 48, 49, 50, etc., contiguous amino acids. In yet further particular nonlimiting examples, the length of the sequence sharing identity is 50 or more amino acids, e.g., 50-55, 55-60, 60-65, 65-70, 70-75, 75-80, 80-85, 85-90, 90-95, 95-100, 100-110, etc. contiguous amino acids.

The extent of identity between two sequences can be ascertained using a computer program and mathematical algorithm. Such algorithms that calculate percent sequence identity generally account for sequence gaps and mismatches over the comparison region or area. For example, a BLAST (e.g., BLAST 2.0) search algorithm (see, e.g., Altschul et al., J. Mol. Biol. 215:403 (1990), publicly available through NCBI) has exemplary search parameters as follows: Mismatch-2; gap open 5; gap extension 2. For protein or polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., *Proc. Natl. Acad. Sci*. USA 85:2444 (1988); Pearson, Methods Mol Biol. 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Ligands and proteins, such as TNF, include additions and insertions, for example, heterologous domains. An addition (e.g., heterologous domain) can be a covalent or non-covalent attachment of any type of molecule. Typically, additions and insertions (e.g., a heterologous domain) confer a complementary or a distinct function or activity.

A nonlimiting example of an addition or insertion is an amino acid spacer, a spacer comprising two or more amino acids and multimers of such spacers comprising two or more amino acids. Nonlimiting examples of amino acid acids that function as amino acids and multimers of spacers include glycine, serine and alanine.

Additions and insertions include chimeric and fusion sequences, which is a protein sequence having one or more molecules not normally present in a reference native (wild type) sequence covalently attached to the sequence. The terms "fusion" or "chimeric" and grammatical variations thereof, means that a portion or part of the molecule contains a different entity distinct (heterologous) from the molecule as they do not typically exist together in nature. That is, for example, one portion of the fusion or chimera, includes or consists of a portion that does not exist together in nature, and is structurally distinct.

In some embodiments, a method for covalently linking TNF ligands to the solid support(s) comprises amine reductive chemistries, cyanogen bromide (CNBr), N-hydroxy succinimide esters, carbonyl diimidazole, reductive amination, 2-fluoro-1-methylpyridinium (FMP) activation, 1-ethyl-3-(3-dimethylaminopropyl)carbodiimide (EDC)-mediated amide bond formation organic sulfonyl chlorides tosyl chloride and tresyl chloride, divinylsulfone, azlactone, cyanuric chloride (trichloror-s-triazine), sulfhydryl reactive chemistries, iodoacetyl and bromoacetyl activation, maleimide, pyridyl disulfide, divinysulfone, epoxy or bisoxiran, TNF-thiol, carbonyl reactive chemistries, hydrazide, reductive amination, hydroxyl reactive chemistries, cyanuric chloride, active hydrogen reactive chemistries, diazonium, mannich condensation, photoreactive cross linking, immobilized serum albumin with CNBr activation, periodate activation, and/or other methods.

In some embodiments, the binding may be ionic binding, electrostatic binding, Van der Waals binding, hydrophobic binding and/or other binding, for example. In some embodiments, an electrostatic bond may be formed between TNF ligands and the one or more solid supports using liking molecules such as immobilized avidin streptavidin and monomeric avidin bound to biotin, antibody-antigen complexes, ligand receptor complexes, and/or other linking molecules.

In some embodiments, the solid support may be formed from materials such as agarose, sepharose, cellulose, pore glass, silica, acrylamide derivatives polyacrylamide beads, trisacryl, sephacryl, an Ultrogel® AcA chromatography sorbent (Pall Corporation), azlactone beads, methacrylate derivatives, a TSKgel® chromatography gel (Tosoh Corporation), a TOYOPEARL® HW polymer gel (Tosoh Corporation), HEMA (2 hydroxyethyl methacrylate, poly (2 hydroxyethyl methacrylate), Eupergit, polystyrene and its derivatives, Poros, polyether sulfone, a polysaccharide, polytetrafluoroethylene, polysulfone, polyester, polyvinylidene fluoride, polypropylene, poly (tetrafluoroethylene-co-perfluoro(alkyl vinyl ether)), polycarbonate, polyethylene, glass, polyacrylate, polyacrylamide, poly(azolactone), polystyrene, polylactide, ceramic, nylon, metal, and/or other materials. In some embodiments, the solid support may be formed by plates, membranes, beads, ceramics, and/or other components.

In some embodiments, the solid support may be or include beads, for example. In some embodiments, capture support 204 comprises ligands bound to beads. As described above, in some embodiments, the ligands may be and/or include sc (single chain)-TNFα ligands. In some embodiments, the ligands may be and/or include a dimeric or trimeric form of the sc-TNF ligand. In some embodiments, the ligands may be and/or include a TNF ligand such as a single-chain polypeptide (sc-TNF) ligand (monomer, dimer or trimer) that binds to, and effectively captures sTNF-Rs from the patient's plasma, for example.

Ligands that have conformational changes due to altered amino acid sequences or purity of the protein might be responsible for substantial changes such as enhancing or reducing binding affinity. Such mutations within the sequence could respectively improve or decrease the binding efficiency of the polypeptide to sTNF-Rs Impurities in TNF preparations would lower the amount of TNF used for coupling by lowering the amount of TNF coupled in proportion to the total amount of protein that is used. These ligands may have high target affinity or binding affinity for this target portion of the patient's biological material. Such binding affinities are represented as $K_D$. (It should be noted that the lower the $K_D$, value, the greater the binding affinity will be.) Representative target affinities of a ligand can be about, for example, greater than about $10^{-6}$ $K_D$, or greater than about $10^{-7}$ $K_D$, or greater than about $10^{-8}$ $K_D$, or greater than about $10^{-9}$ $K_D$, or greater than about $10^{-10}$ $K_D$, or greater than about $10^{-11}$ $K_D$, or greater than about $10^{-12}$ $K_D$, or greater than about $10^{-13}$ $K_D$. The affinity of TNF for sTNF-R1 may be approximately $10^{-11}$ $K_D$, for example. The affinity of TNF for sTNF-R2 may be approximately $10^{-10}$ $K_D$, for example.

In some embodiments, the sc-TNF ligands comprise sc-TNFα molecules. In some embodiments, the sc-TNF ligands comprise a TNFα monomer, one or more complexes of TNFα proteins, and/or other components. In some embodiments, the complexes comprise dimers, trimers, multimers, muteins, and/or fragments thereof. In some embodiments, capture support 204 may comprise sc-TNF protein ligands conjugated to a plurality of agarose beads (e.g., which selectively bind to sTNF-Rs present in the plasma that is circulated through system 10, e.g. as shown in FIG. 1-3).

In some embodiments, generation of sc-TNF (and/or other ligands) may be performed through various means of genetic engineering and protein expression (see, for example, Muller, R., et al. (1986) FEBS Lett 197, 99-104; Mori, T., et al. (1994) Gene 144, 289-293; Horwitz, A. H., et al. (1996) Protein Expr Purif 8, 28-40; Li, H., et al. (2019) World J Microbiol Biotechnol 35, 27; Ashman, K., et al. (1989) Protein Eng 2, 387-391; Su, X., et al. (1992) Biotechniques 13, 756-762; Li, C. B., et al. (1992) Sci China B 35, 319-328; Guo, D., et al. (1995) Biochem Biophys Res Commun 207, 927-932; Xiang, J., et al. (1997) J Biotechnol 53, 3-12 Tang, P., et al. (1996) Biochemistry 35, 8216-8225).

The ligands may have a given density and orientation on a given support (such as a bead, for example). The ligands can be covalently linked to the beads (and/or other supports) through amines or thiol moieties, for example. The density and orientation may be configured to enhance binding between the ligands and the target component of the body fluid. In some embodiments, the ligands may be configured such that they extend out from the support matrix (e.g., a given bead) at the amino (N) or carboxyl (C) terminal for binding accessibility. In some embodiments, a linker may be placed between the bead (for example) surface and the ligand to extend the ligand into the body fluid passing through as a means of reducing steric hindrance that would interfere with the binding.

The density can be expressed in milligrams ligand per milligrams of support. In some embodiments, the ligand may be a 54-$K_D$ protein. By way of example and without limitation, the support may have a ligand density of at least about 0.1 mg ($1.8\times10^{-6}$ mmoles) ligand/mg of support (e.g., beads), at least about 1 mg ($18\times10^{-6}$ mmoles) ligand/mg of support (e.g., beads), at least about 5 mg ligand/mg of support (e.g., beads), at least about 7 mg ($1.3\times10^{-4}$ mmoles) ligand/mg of support (e.g., beads), at least about 10 mg ligand/mg of support (e.g., beads), at least about 15 mg ligand/mg of support (e.g., beads), or at least about 20 mg ligand/mg of support (e.g., beads), or more, for example.

A size, number, density, and/or concentration of a support, such as a bead or beads (e.g., in combination with a shape and size of housing 16), may be configured to facilitate a laminar flow of the blood, plasma, and/or other body fluid through the beads to enhance the binding between the ligands and the target component of the body fluid. Increasing a bead size may proportionally accommodate higher flow rates. Increasing the density of the coupled ligand may increase the capture capacity while avoiding concentrations that may contribute steric hindrance which would interfere with effective binding of the target molecule. The size, number, density, orientation and/or concentration of the support (e.g., beads) may facilitate a flow-rate of plasma, for example, through system 10 that effectively balances tradeoffs between capture rates and clinically practical procedure times. For example, a plasmapheresis procedure involving one embodiment of system 10 may require circulation of two patient plasma volumes through the sequestering chamber 202 to achieve a specific target concentration reduction of sTNF-R1/R2 from the patient's plasma; whereas an alternative embodiment with twice the capture rate efficiency as the first embodiment may only require the circulation of one patient plasma volume through its sequestering chamber to achieve comparable sTNF-R1/R2 concentration reduction, thereby reducing the clinical procedure time by about a factor of two. In some embodiments, the beads may include one or more different bead materials such as commercially available agarose or polyacrylamide compositions.

In some embodiments, the beads and/or other solid support may have a size that prevents them from passing through filters 212 and 214 (see filter pore size discussion herein). In some embodiments, the beads may be quenched (where the binding sites that are left after TNF coupling are saturated in their occupancy) with ethanolamine or ethylene diamine to enhance binding specificity. Ethanolamine may be used as a quenching agent, for example, due to its biocompatibility profile. In some embodiments, the beads may be pretreated with agents such as immulons, polystyrenes or polyethylenes, in order to better control and maximize recovery (or for other reasons), and/or the beads may be pre-treated with a commercially available cross-linker. A cross-linker may be any chemical or substance used to facilitate the attachment to the solid phase of the molecule that captures one or more circulating immune complexes. Non-limiting examples of commercially available cross-linkers are poly-L-lysine, glutaraldehyde, and cyanogen bromide, for example.

In some embodiments, the beads may form a binding matrix, which may include covalently or non-covalently bound affinity molecules (e.g., as described herein). In some embodiments, the beads may be in the range of about 20-1,000 μm in diameter, for example. In some embodiments, the beads may be in the range of about 25-500 μm in diameter. In some embodiments, the beads may be in the range of about 25-200 μm in diameter. In some embodiments, the beads may be in the range of about 40-180 μm in diameter. In some embodiments, the beads may be in the range of about 50-170 μm in diameter. In some embodiments, the beads may be in the range of about 65-160 μm in diameter. In some embodiments, the beads may be in the range of about 75-150 μm in diameter.

The beads may be formed from materials which are biocompatible and to which various ligands are covalently linked or electrostatically bound (e.g., as described above). Binding of ligands may be performed using covalent binding methods such as amine reductive chemistries, cyanogen bromide (CNBr), N-hydroxy succinimide esters, carbonyl diimidazole, reductive amination, FMP activation, EDC-mediated amide bond formation, organic sulfonyl chlorides tosyl chloride and tresyl chloride, divinylsulfone, azlactone, cyanuric chloride (trichloro-s-triazine), sulfhydryl reactive chemistries, iodoacetyl and bromoacetyl activation methods, maleimide, pyridyl disulfide, divinylsulfone, epoxy or bisoxiran, TNF-Thiol, carbonyl reactive chemistries, hydrazide, reductive amination, hydroxyl reactive chemistries, cyanuric chloride, active hydrogen reactive chemistries, diazonium, Mannich condensation, photoreactive cross linking, and/or other operations. Coupling can also be done using immobilized serum albumin with CNBr activation or periodate activation. In some embodiments, binding may be performed using non-covalent interactions such as a) immobilized avidin streptavidin and monomeric avidin bound to biotin; b) antibody-antigen complexes; and/or c) ligand-receptor complexes.

In some embodiments, a capture efficiency, equivalent to [1−(sTNF-R plasma concentration at outlet 210/sTNF-R plasma concentration at inlet 200)]×100 and thus expressed as a percentage, of capture support 204 binding to the target component may be at least 10% or more sTNF-R1 and/or sTNF-R2. In some embodiments, the capture efficiency may be at least 50% or more. In some embodiments, the capture efficiency may be at least 80% or more. In some embodiments, the capture efficiency may be at least 90%, 95%, 96%, 97%, 98%, 99%, or more.

Capture efficiency values may take into consideration a time-based component (e.g., a capture efficiency over the first 5, 10, 15, 30, 45, 60, 90, 120 or more minutes of a treatment) since available binding sites within the system's capture matrix decrease as more target agents are cumulatively captured within the column (system 10). By way of several non-limiting examples, in some embodiments, at least 80% or more of sTNF-R proteins (sTNF-R1 and/or sTNF-R2) in a flowing biological sample may become bound to TNF ligands within sequestering chamber 202 within about 30 minutes, for example. In some embodiments, at least 90% or more of sTNF-R proteins (sTNF-R1 and/or sTNF-R2) in a flowing biological sample may become bound to TNF ligands within sequestering chamber 202 within about 30 minutes. In some embodiments, at least 95% or more of sTNF-R proteins (sTNF-R1 and/or sTNF-R2) in a flowing biological sample may become bound to TNF ligands within sequestering chamber 202 within about 30 minutes. In some embodiments, at least 96% or more of sTNF-R proteins (sTNF-R1 and/or sTNF-R2) in a flowing biological sample may become bound to TNF ligands within sequestering chamber 202 within about 30 minutes. In some embodiments, at least 97% or more of sTNF-R proteins (sTNF-R1 and/or sTNF-R2) in a flowing biological sample may become bound to TNF ligands within sequestering chamber 202 within about 30 minutes. In some embodiments, at least 98% or more of sTNF-R proteins (sTNF-R1 and/or sTNF-R2) in a flowing biological sample may become bound to TNF ligands within sequestering chamber 202 within about 30 minutes. In some embodiments, at least 99% or more of sTNF-R proteins (sTNF-R1 and/or sTNF-R2) in a flowing biological sample may become bound to TNF ligands within sequestering chamber 202 within about 30 minutes.

Although not wanting to be bound by any theory, the capture efficiency values described herein may result from the use of the sc-TNF ligand described above (e.g., which has exceptionally high target affinity), the use of the trimeric form of the sc-TNF ligand, the purity of the ligand, the ligand density on the beads, the ligand binding orientation on the beads, the size of the beads, the number, density and concentration of the beads in system 10, a flow-rate through system 10 that balances capture efficiency versus clinical procedure time, the physical size and structure of housing 16 which yields the laminar flow through the beads, the (e.g., chemistry and/or electrostatic) process used for coupling the ligands to the beads, the sterilization technique and radiation dosage, and/or other factors. Put another way (again not wanting to be bound by any theory), one reason, for example, the efficiency of the column (system 10) is high may be due to the large amount of capture ligand on the bead matrix in conjunction with the high binding efficiency of the ligand.

In some embodiments, the high binding specificity and/or affinity of capture support 204 to the target component may be because the only known interaction of the capture ligand is exclusive to sTNF-R1 and/or sTNF-R2 in the plasma. This binding specificity may result from the use of the sc-TNF ligand described above, the trimeric form of the sc-TNF ligand, the materials used to form (e.g., the chemical composition of) the beads and/or the specific bead matrix, use of ethanolamine to quench the beads (e.g., used to reduce non-specific binding), optimization of target protein binding versus non-specific binding, the pore size used for filters 212 and 214, and/or other factors.

In some embodiments, a binding affinity of the capture support to the at least one target component is at least about $10^{-5}$ $K_D$ or greater. In some embodiments, a binding affinity of the capture support to the at least one target component is at least about $10^{-6}$ $K_D$. In some embodiments, a binding affinity of the capture support to the at least one target component is at least about $10^{-7}$ $K_D$. In some embodiments, a binding affinity of the capture support to the at least one target component is at least about $10^{-8}$ $K_D$. In some embodiments, a binding affinity of the capture support to the at least one target component is at least about $10^{-9}$ $K_D$. In some embodiments, a binding affinity of the capture support to the at least one target component is at least about $10^{-10}$ $K_D$. In some embodiments, a binding affinity of the capture support to the at least one target component is at least about $10^{-11}$ $K_D$. In some embodiments, a binding affinity of the capture support to the at least one target component is at least about $10^{-12}$ $K_D$. In some embodiments, a binding affinity of the capture support to the at least one target component is at least about $10^{-13}$ $K_D$. In some embodiments, a binding affinity of the capture support to the at least one target component is at least about $10^{-14}$ $K_D$.

In some embodiments, system 10 may be configured such that it has a leach rate of TNF less than $1/1000^{th}$ of maximum tolerable daily dose (MTD) limits (see, for example, Goossens, V., et al. (1995) Proc. Natl Acad. Sci. USA, 92, 8115-8119). In some embodiments, system 10 may be configured such that it has a leach rate less than $1/10000^{th}$ of MTD dose limits. In some embodiments, system 10 may be configured such that it has a leach rate less than $1/500^{th}$ of MTD daily limits. In some embodiments, system 10 may be configured such that it has a leach rate less than $1/100^{th}$ of MTD daily limits. This may ensure the clinical effectiveness of system 10 including successful, efficient, and specific capture of the one or more target components, unbiased by clinical effects and/or side effects resulting from escape (i.e., leaching) of portions of capture support 204 (e.g., the ligands described herein) into the patient's circulatory system.

Leach rate may be defined as the percent of capture support 204 that escapes system 10 (e.g., in units of ng/mL/min) relative to the total volume of capture support 204 contained in system 10's sequestering chamber 202 following production. For example, in some embodiments, system 10 may have a leach rate of less than about 150 ng/mL/min. In some embodiments, system 10 may have a leach rate of less than about 100 ng/mL/min. In some embodiments, system 10 may have a leach rate of less than about 80 ng/mL/min. In some embodiments, system 10 may have a leach rate of less than about 50 ng/mL/min. In some embodiments, system 10 may have a leach rate of less than about 40 ng/mL/min. In some embodiments, system 10 may have a leach rate of less than about 30 ng/mL/min. In some embodiments, system 10 may have a leach rate of less than about 20 ng/mL/min. In some embodiments, system 10 may have a leach rate of less than about 10 ng/mL/min.

The leach rate may result from the strength and integrity of the (e.g., chemical and/or electrostatic) bonding between the sc-TNF ligands and the beads, the use of reductive amination chemistry with a specific ligand, the use of the trimeric form of the sc-TNF ligand, the (e.g., chemistry and/or electrostatic) process used for coupling the ligands to the beads, the clinical pretreatment approach for preparing system 10 for patient treatment (e.g., volume and flow-rate of pre-use flushing), a clinically-practical flow-rate through system 10 that balances capture efficiency versus clinical procedure time, cleaning housing 16 during manufacturing, the sterilization technique and radiation dosage utilized in production, and/or other factors. In some embodiments, the clinical pretreatment preparation of system 10 (e.g., volume and flow-rate of pre-use flushing) comprises a one-liter flush of normal saline at a flow rate of about 100 mL/min.

Figure 4:
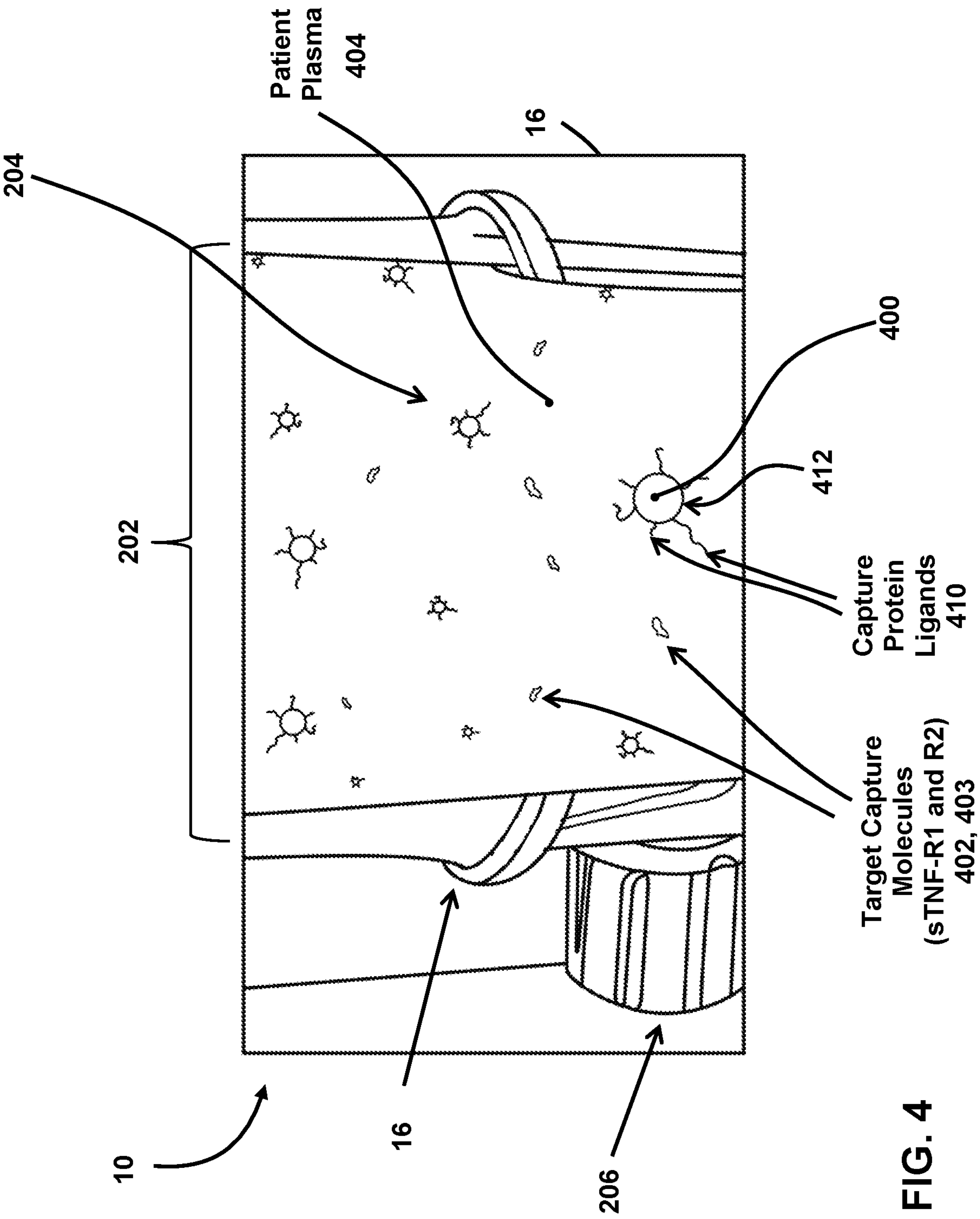
FIG. 4 illustrates a capture support (e.g., ligand coated beads in this example) in a sequestering chamber of a housing of the system binding to a target component of body fluid (plasma in this example) to capture the target component in the sequestering chamber, in accordance with one or more embodiments.
Figure 5:
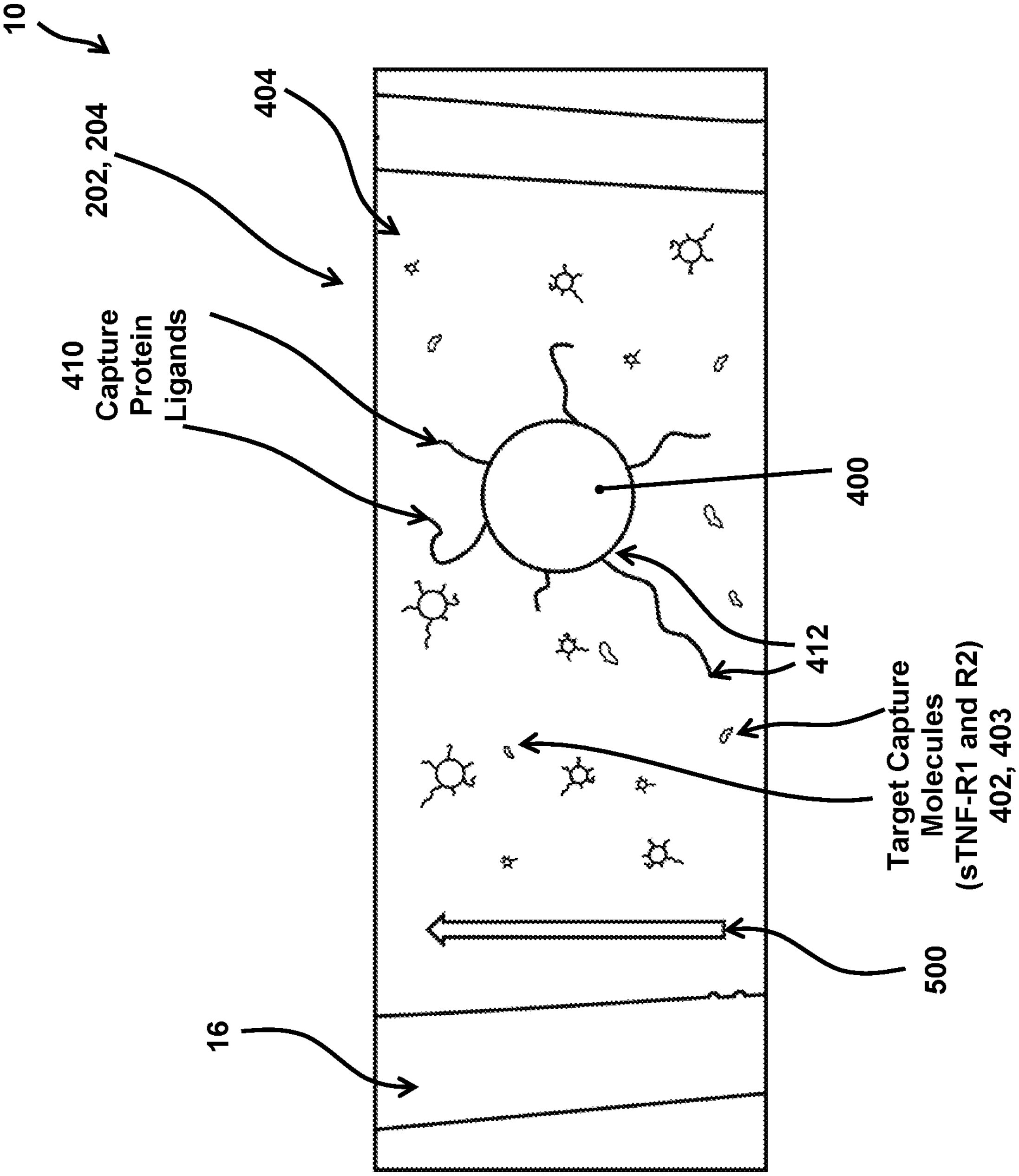
FIG. 5 is an enlarged view of the capture support shown in FIG. 4, in accordance with one or more embodiments. The enlarged view shows the capture support comprising a bead and capture ligands.

By way of a non-limiting example, FIG. 4 and FIG. 5 illustrate capture support 204 (e.g., beads 400 in this example) in sequestering chamber 202 of housing 16 binding to a target component 402 (sTNF-R1) and/or a second target component 403 sTNF-R2 (these are just examples—more target components are possible) of body fluid (plasma 404 (comprised of sTNF-R1 402 and sTNF-R2 403) in this example) to capture target component 402 and 403 within the sequestering chamber 202. FIG. 5 is an enlarged view of a bead 400 (e.g., a portion of the capture support) shown in FIG. 4. FIG. 5 shows the direction 500 of body fluid (e.g., plasma 404) flow through system 10 (FIG. 1-3) from inlet 200 to outlet 210 (FIG. 1-3). In some embodiments, system 10 may be symmetrical and may be bidirectional such that a clinical user could select to use either end of the apparatus to serve as the upstream inlet or downstream outlet.

As shown in FIG. 4 and FIG. 5, the capturing occurs when there is contact between capture support 204 and the body fluid (plasma 404). Specifically, the capturing occurs responsive to close proximity and/or direct contact between the sTNF-R1 and sTNF-R2 molecules 402, 403 in plasma 404 and ligands (e.g., the sc-TNF ligands described above) 410 that are bound (coupled) to beads 400. Bonds 412 between ligands 410 and beads 400 are also shown. Capture support 204 (e.g., the combination of beads 400 and ligands 410) may be configured to bind to one or more target components 402, 403 (sTNF-R1 and R2 molecules) to reduce an amount of one or more target components 402, 403 in the body fluid (e.g., plasma 404).

In some embodiments, once the treated sTNF-R deficient plasma passes through outlet 210 (FIG. 2 and FIG. 3), some or all of the treated sTNF-R deficient sample may be reinfused into the patient (e.g., via the apheresis machine shown in FIG. 1). As sTNF-Rs are removed, the reservoir of uncomplexed sTNF-Rs in the patient's blood is reduced, resulting in a concentration equilibrium shift toward increased availability of TNF to promote anti-cancer effects at the tumor site(s).

As described herein, system 10 (FIG. 1-3) may be configured to selectively remove immune suppressive factors associated with states of immune suppression. In some embodiments, the immune suppressive factors are soluble TNF receptor 1 and soluble TNF receptor 2 (sTNF-Rs). Removing sTNF-Rs from the patient's blood, plasma, and/or other body fluid may result in increased availability of endogenous TNF, which promotes anti-cancer effects at tumor site(s).

Returning to FIG. 2 and FIG. 3, access ports 206, 208 may be configured to provide access to sequestering chamber 202. This access may be separate from access via inlet 200, outlet 210, and/or other access points. Access ports 206 and 208 may be configured to facilitate insertion and/or removal of capture support 204 to or from sequestering chamber 202. This may be performed during manufacturing of system 10, for example, and/or at other times.

In some embodiments, capture support 204 may be suspended in a preservative buffer solution for storage prior to use in system 10. In some embodiments, the preservative buffer solution comprises bacteriostatic saline, bacteriostatic phosphate, and/or other solutions. In some embodiments, the preservative buffer solution may be bacteriostatic phosphate buffered saline (PBS) that may contain 0.9% benzyl alcohol. Capture support 204 may be refrigerated in solution at 2-8° C. until ready for subsequent aseptic filling of housing 16. In some embodiments, system 10 may be stored at 2-8° C. between its time of manufacture, shipping, and/or clinical use.

In some embodiments, the preservative buffer solution is flushed from system 10 (e.g., via inlet 200 and outlet 210) immediately prior to clinical use of system 10. In some embodiments, access ports 206, 208 comprise Luer fittings having caps and/or other components. In some embodiments, access ports 206 and/or 208 have corresponding caps and/or other components. The corresponding caps may be formed from polycarbonate and/or other materials.

Figure 6:
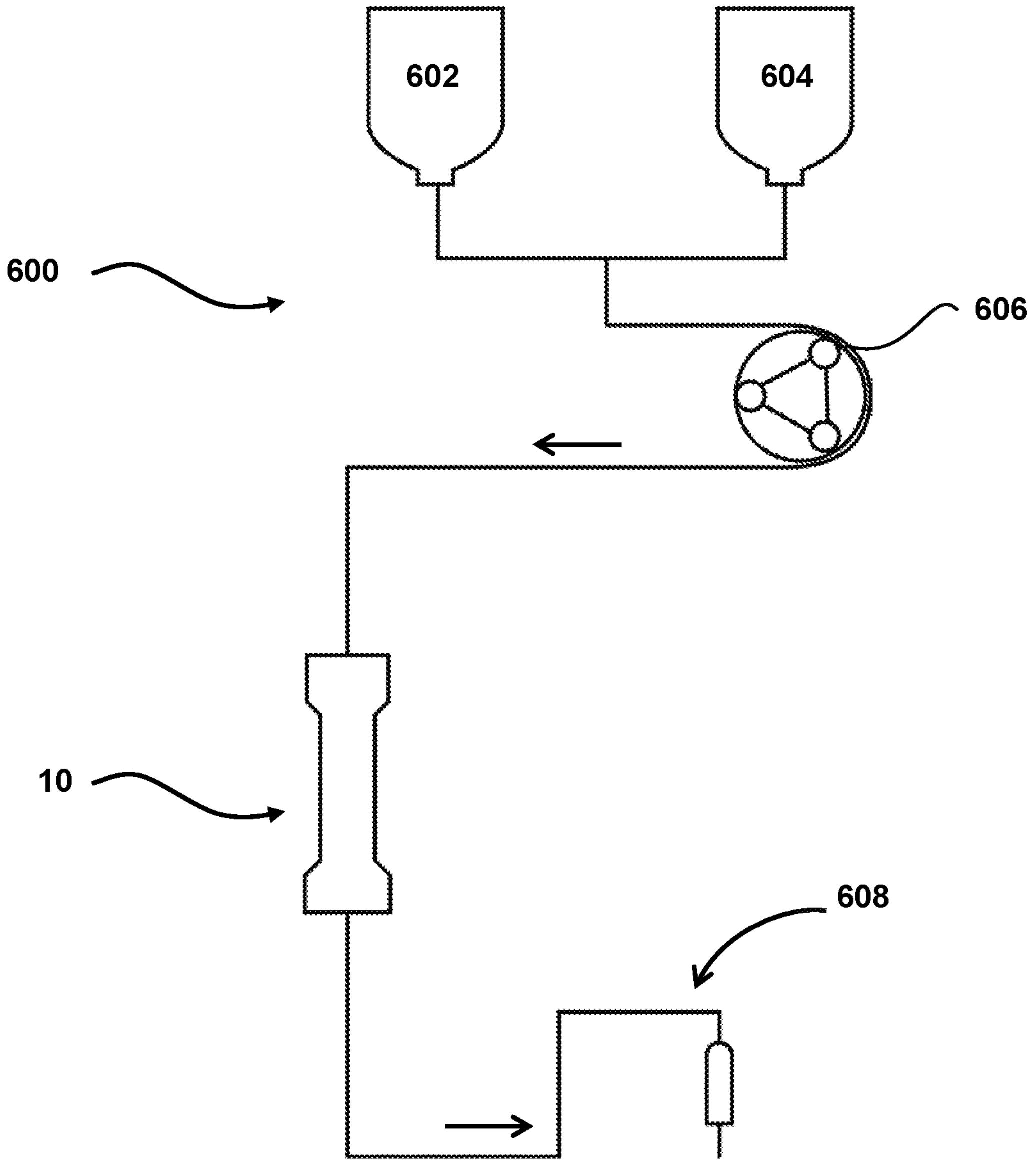
FIG. 6 illustrates an example regeneration mechanism, in accordance with one or more embodiments.

FIG. 6 illustrates an example regeneration mechanism 600 configured to couple with system 10. In some embodiments, regeneration mechanism may be considered to be an additional part of, and/or an extension of system 10. As shown in FIG. 6, mechanism 600 may include a rinsing solution 602 source, a regeneration solution 604 source, a pump 606, a waste line 608, and/or other components. In some embodiments, rinsing solution 602 and regeneration solution 604 may be alternately pumped through system 10 by pump 606 and into waste line 608.

In some embodiments, system 10 may include a target component outlet port configured to facilitate sampling or removal of all or part of the captured target component (e.g., without compromising the extracorporeal closed-circuit column formed by system 10).

In some embodiments, system 10 may be configured to facilitate reuse by alternating capture and dissociation steps. Dissociating the target prior to further capture may regenerate the column to about the original specifications and function. To accomplish this dissociating, the captured complexes between bead-bound proteins and their ligands is disrupted, resulting in a dissociated complex. Such a dissociation stage may be application dependent so the particular dissociation conditions may depend upon the particular subtype of circulating protein or complexed moiety that was captured. Agents that cause high salt concentrations, such as chaotropic agents or low pH may be effective dissociation agents. In order to dissociate the capture complex high salt, such as sodium chloride (300 mM-1,5M) or a chaotropic agent such as guanidine hydrochloride 3-8M, concentrations may be used. In some embodiments, a salt solution may have a pH of approximately 7.2 and comprise either 500 mM NaOH, 2 mM EDTA and 50 mM Tris buffer, or 500 mM NaOH, 2 mM EDTA and 50 mM sodium phosphate. Alternatively, the captured immune complexes may be dissociated with a low pH solution. The effective pH for the dissociation stage may be approximately 2.8, for example. An example pH range may be 1.5 to 2.5. This may be accomplished with pH adjusted citrate or glycine solutions. In some embodiments, the pH range may be 2.0 to 2.5. In some embodiments, the pH range may be about 2.5-3.5. However, it should be realized that the lower the pH, the shorter the dissociation time needed. Acids, such as acetic acid, citric acid and hydrochloric acid, for example, may be used for lowering the pH. In addition to either raising the salt concentration or lowering the pH, other methods of dissociating immune complexes are also possible. In addition to either raising the salt concentration or lowering the pH, the dissociation conditions may be configured to occur for a short period of time and include bovine serum albumin (BSA) and/or other ligand or receptor competing components.

In some embodiments, system 10 may include an elution reagent port configured to facilitate introduction of an elution reagent into the sequestering chamber (e.g., without compromising the extracorporeal closed-circuit column formed by system 10). The elution reagent port may be further configured to receive a conditioning agent configured to prepare system 10 for reuse. In some embodiments, the elution reagent port(s) may be the same as one or both of access ports 206 and/or 208.

In some embodiments, pump 606 may be configured to drive the elution/regeneration agents through inlet 200 (FIG. 2), sequestering chamber 202 (FIG. 2), and outlet 210 (FIG. 2). Pump 606 may comprise a syringe pump, a peristaltic pump, a piston pump, a diaphragm pump, a combination thereof, and/or other pumps.

Figure 7:
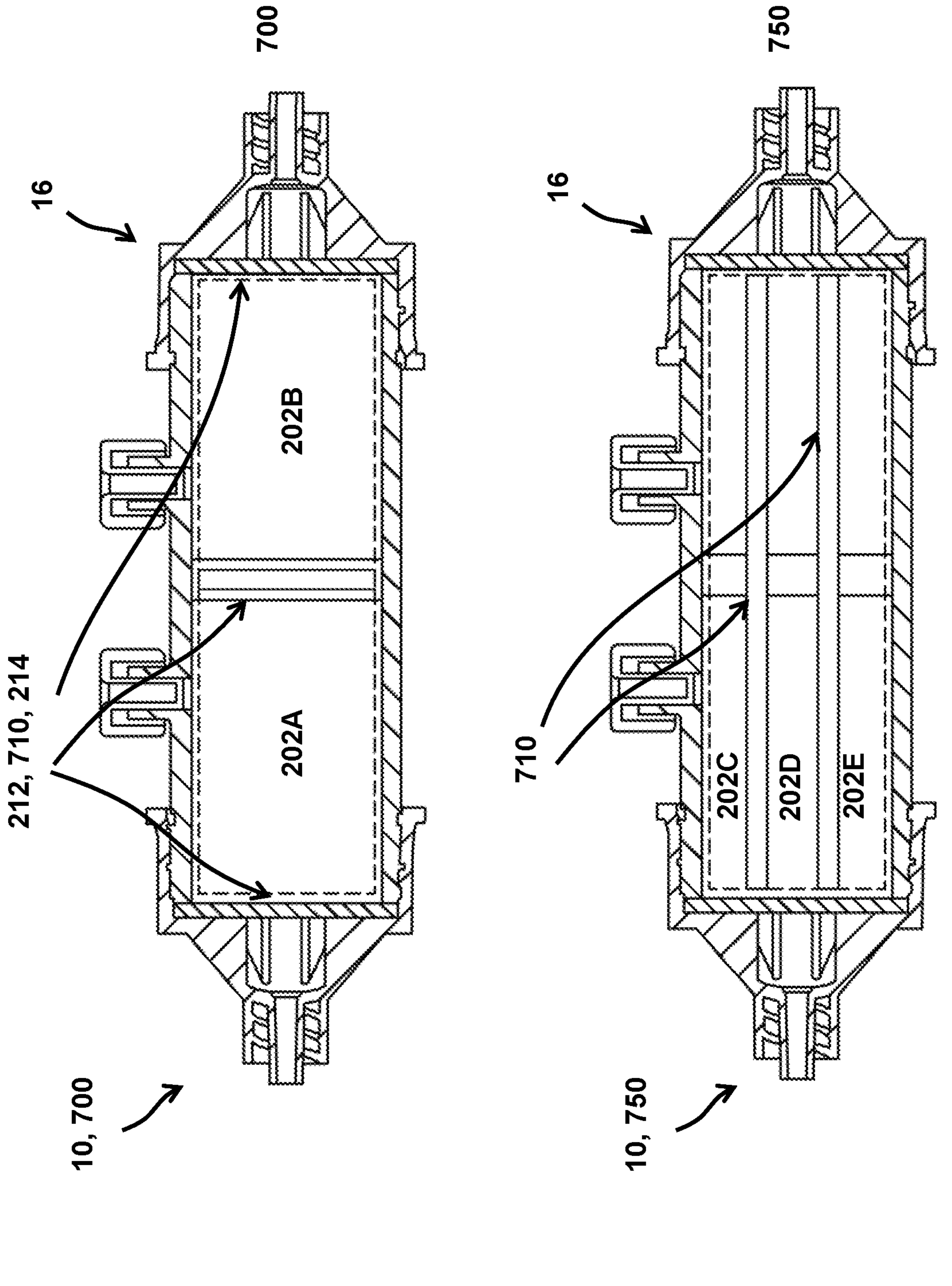
FIG. 7 illustrates example embodiments where the system includes two or more internal sequestering chambers, which can be configured in series or parallel relative to fluid flow from inlet to outlet, in accordance with one or more embodiments.

In some embodiments, system 10 may comprise one or more additional sequestering chambers 202, as depicted in FIG. 7. FIG. 7 illustrates two example embodiments 700 and 750 of system 10 having the additional sequestering chambers 202. In example embodiment 700, sequestering chambers 202A and 202B are positioned within housing 16 in series. In example embodiment 750, chambers 202C, 202D, and 202E are positioned within housing 16 in parallel. The different chambers (e.g., 202A and B, and 202 C-E) may be separated by filters 212, 214 (and/or other filters), separating membranes 710, and/or other components. In some embodiments, separating membranes 710 may be filters 212 and/or 214 and vice versa, for example.

These additional sequestering chambers 202A-E may include capture supports similar to and/or the same as capture support 204 (FIG. 2) described above, or different capture supports. The additional sequestering chambers 202 (A-E) and capture supports may be configured to function similar to and/or the same as sequestering chamber 202 and capture support 204. In some embodiments, the one or more additional sequestering chambers (202A-E) may be combined (e.g., 202A and B, and 202C, D, and E) to form a multistage separation circuit configured to bind with a plurality of different target components. In some embodiments, the multiple sequestering chambers may be configured in a serial configuration (e.g., embodiment 700) where the full volume of body fluid (plasma, for example) flowing through system 10 passes sequentially through each of the plurality of sequestering chambers (e.g., 202A then 202B). In some embodiments, the multiple sequestering chambers may be configured in a parallel configuration (e.g., embodiment 750) where the volume of body fluid (plasma, for example) flowing through system 10 is distributed into equal or nonequal fractions such that these fractionated subvolumes of fluid are passed in parallel through each of the plurality of sequestering chambers (e.g., 202C, 202D, and 202E).

Figure 8:
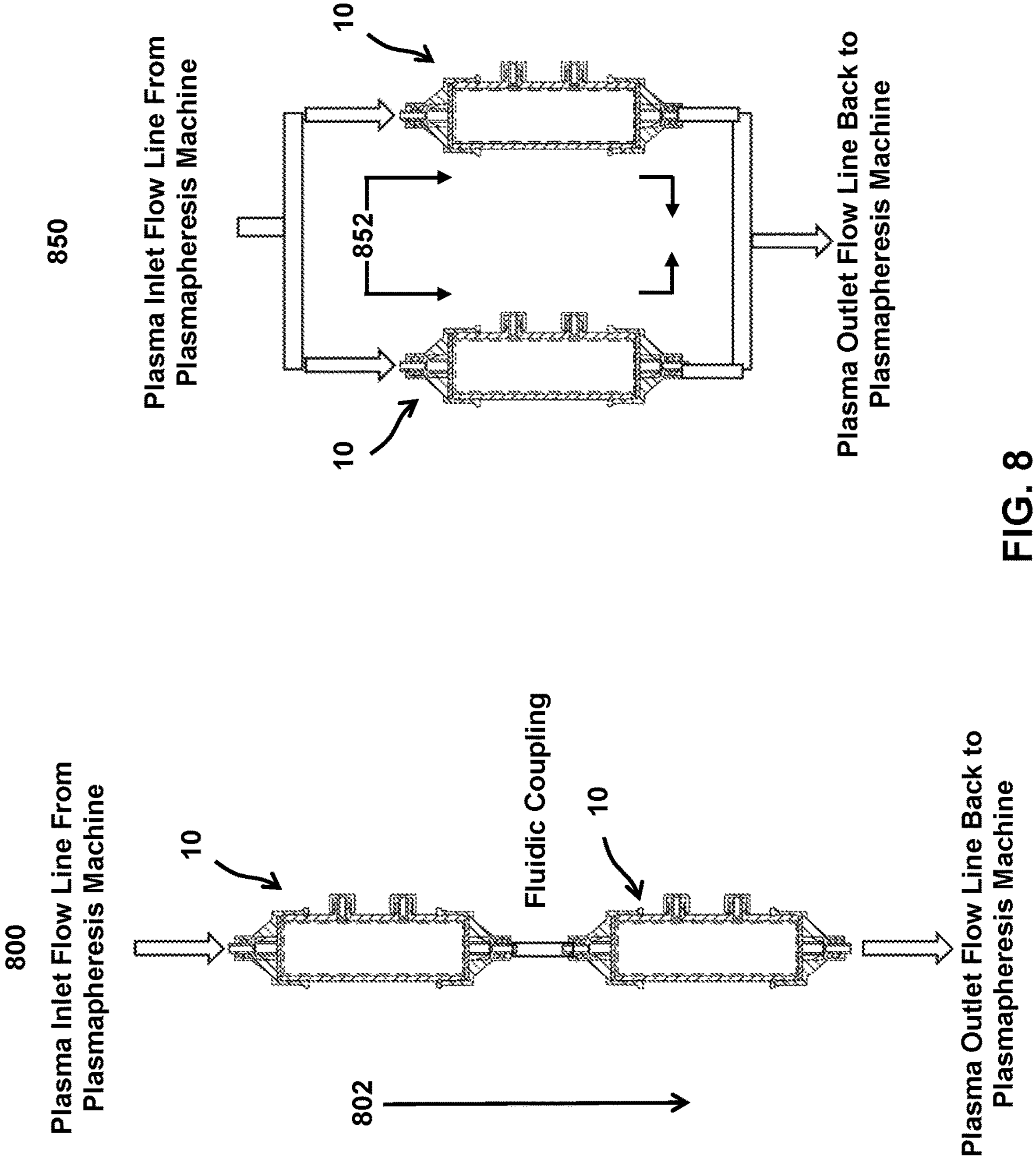
FIG. 8 illustrates example methods of use where multiple systems can be utilized in series and/or parallel configurations within a single plasmapheresis flow circuit, in accordance with one or more embodiments.

FIG. 8 illustrates additional embodiments 800 and 850 where a plurality of systems (e.g., a plurality of system 10's) may be configured into a single plasmapheresis flow circuit 802 or 852 at the same time during a treatment procedure.

In one embodiment (e.g., 800), the plurality of systems (10) may be cascaded in series where, plasma for example, flows through one system 10 and then next. In another embodiment (e.g., 850), two or more systems (10) may be configured in parallel where the volume of body fluid (plasma, for example) flowing through the plasmapheresis flow circuit may be distributed into equal or nonequal fractions such that these fractionated sub-volumes of fluid may be passed in parallel through each of the plurality of systems (e.g., two systems 10 are shown in embodiment 850 but this is not intended to be limiting). In one embodiment involving such a parallel system configuration, the total volume of fluid in the plasmapheresis flow circuit may be initially directed to pass through one or more of the parallel system sequestering chambers (e.g., 202 as described above), and then at a subsequent time during the same treatment procedure, fluid in the circuit may be redirected to pass through a different system or subdivided to pass through a different combination of the parallel systems coupled within the flow circuit. In any of the configurations described above, each individual system may contain the same or different capture matrices targeted at the same or different target agents in the body fluid.

Figure 9:
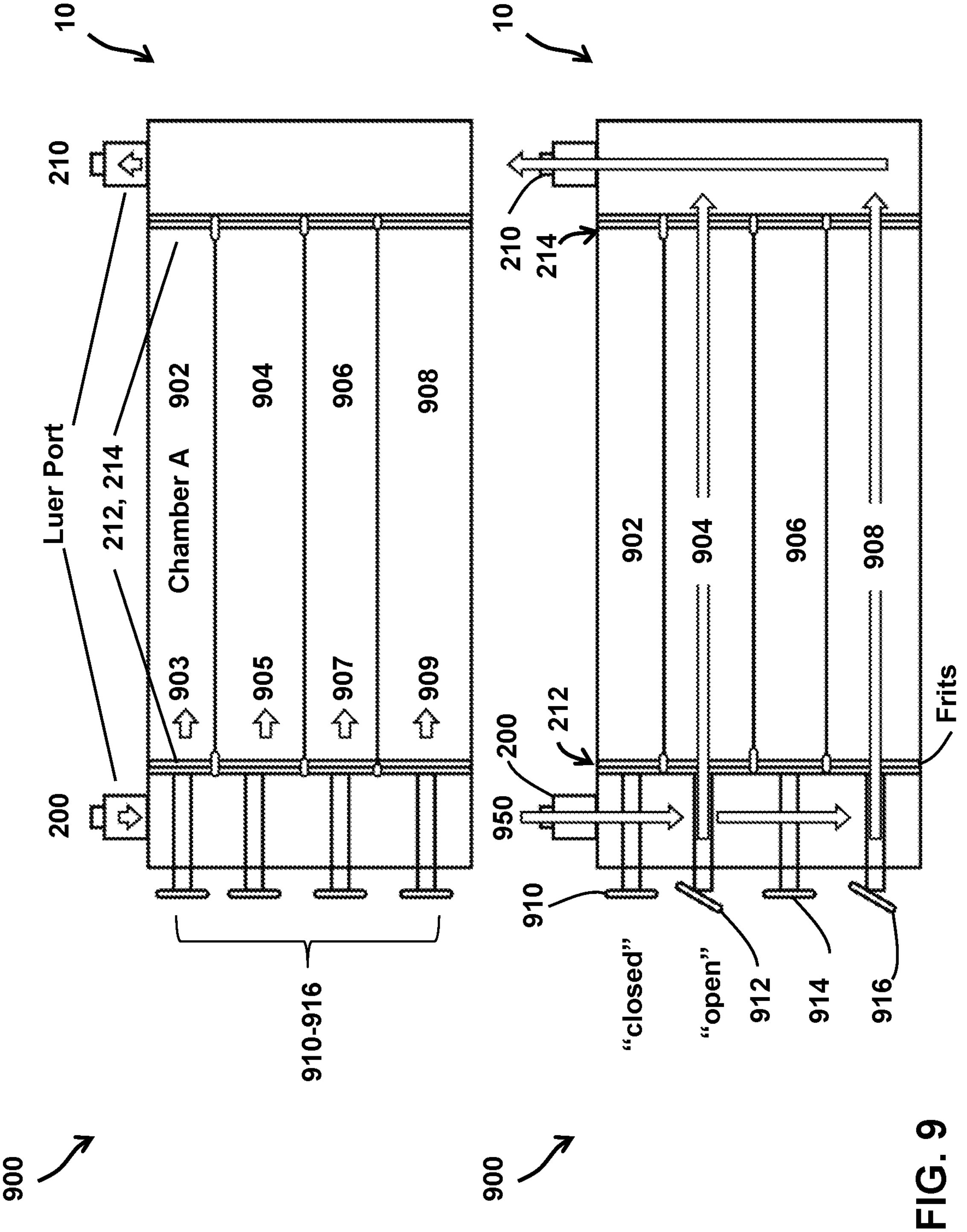
FIG. 9 illustrates multiple sequestering chambers, each with independently controllable flow valves, in a single housing, in accordance with one or more embodiments
Figure 10:
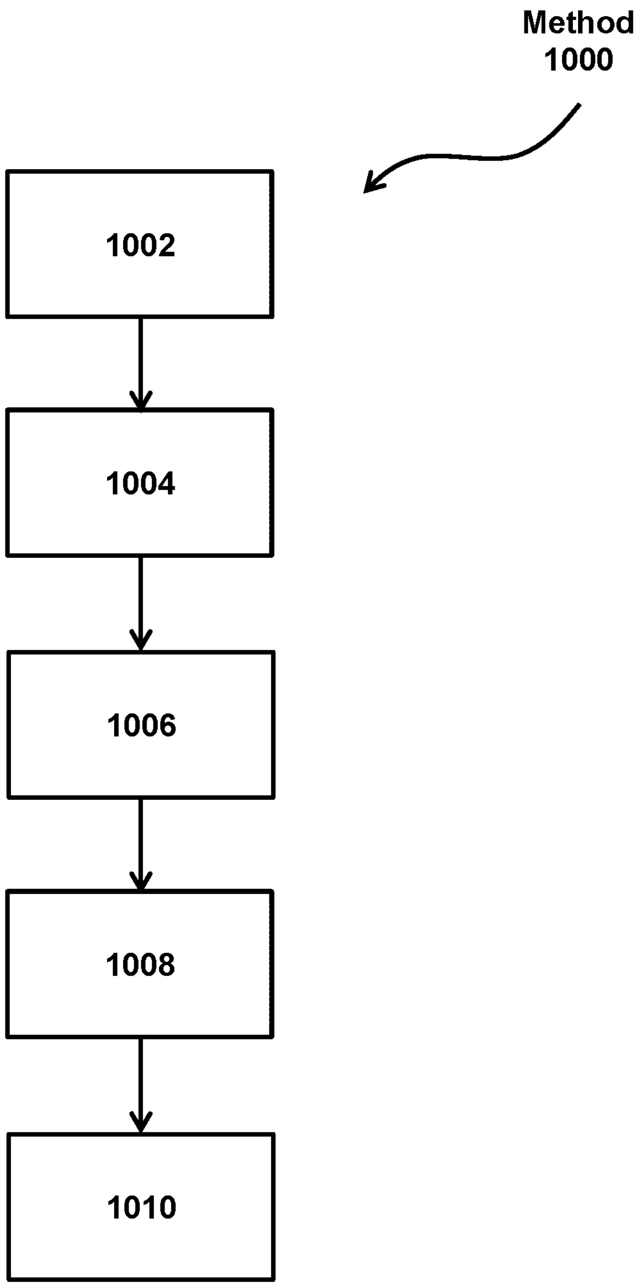
FIG. 10 illustrates a method for removing the target component of the blood, plasma, and/or other body fluid with the system, in accordance with one or more embodiments.

FIG. 9 illustrates an embodiment 900 of system 10 comprising fluid inlet 200 for the fluid to enter system 10, multiple sequestering chambers 902, 904, 906, and 908 in parallel, each with an independent flow path (903-909) from system 10 inlet 200 to outlet 210 (which may be formed by male Luer ports for example), and each with its own flow control valve 910, 912, 914, 916 (e.g., stopcocks and/or other components) allowing an individual sequestering chamber to be turned "on" or "off". In this embodiment, fluid can be directed through any one chamber or any combination of multiple chambers at the same time. An example flow path 950 is shown in the bottom portion of FIG. 9. Fluid existing the one or more chambers being used at a time, is recombined at the system fluid outlet 210 for return to the apheresis machine. Within this embodiment, each sequestering chamber 902-908 can include one or more different capture molecules (e.g., included in capture support 204 described above) configured to target one or more different target portions in the body fluid. As shown in FIG. 10, the plurality of sequestering chambers 902-908 and their corresponding flow control valves 910-916 may be included within a single, unitary outer housing (e.g., 16 as described above).

FIG. 10 illustrates method 1000 for removing the target component of the blood, plasma, and/or other body fluid with system 10 (FIG. 1-3). The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 10 and described below is not intended to be limiting.

At an operation 1002, blood, plasma, and/or other body fluid may be conducted from a patient (e.g., patient 14 shown in FIG. 1) through inlet 200 (FIG. 2-3) to sequestering chamber 202 (FIG. 2-3).

At an operation 1004, the target component of the blood, plasma, and/or other body fluid may be bound to capture the target component in sequestering chamber 202 (FIG. 2-3) to reduce the amount of the target component in the blood, plasma, and/or other body fluid.

At an operation 1006, the body fluid having the reduced amount of the target component is passed from sequestering chamber 202 (FIG. 2-3) through outlet 210 (FIG. 2-3) for reintroduction back into the patient.

At an operation 1008, the reduced amount of the target component in the body fluid reintroduced back into the patient where it may or may not be quantitatively measured (e.g., operation 1008 may be optional). In some embodiments, where quantitative measuring is used, the measuring may comprise one or more of performing liquid chromatography-mass spectrometry (LC-MS), high performance liquid chromatography (HPLC), ultra-high performance liquid chromatography (UHPLC), resistance measurements, light emission measurements, chemiluminescence, electroluminescence, electrochemiluminescence, chromatographic monitoring, positron emission tomography (PET), x-ray computed tomography (CT), magnetic resonance imaging (MRI), ultrasound, gamma camera, single photon emission computed tomography (SPECT), an enzyme linked immunosorbent assay (ELISA), surface plasmon resonance (SPR) measurements, and/or other operations.

At an operation 1010, a leach rate of the capture support in the body fluid reintroduced back into the patient may or may not be measured (e.g., operation 1010 may be optional). The concentration of the capture agent (TNF, for example) may be determined from fluid samples drawn from the inlet 200 and the outlet 210 and/or from fluid connectors attached thereto. The difference between the two measured concentration values may be used to determine the rate and amount of capture agent escaping the sequestering chamber. In some embodiments, flow rate in mL/min may be utilized to determine the total amount of capture agent leached from the system and into the patient's circulatory system over a period of time (the duration of a single treatment procedure, for example).

Although the system(s) or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

The following appended examples provide various demonstrations of successful use of various embodiments of the systems and methods described herein.

Example 1—Materials and Assembly of the Present System

MATERIALS—The immobilized solid support matrix (capture support 204) utilized in this embodiment of the system was an agarose-based bead (i.e., a strong crosslinked support resin).

CHEMISTRIES—The solid support matrix (capture support 204) was activated using sodium metaperiodate, which was then coupled to a single chain TNF ligand by reductive amination. The amount of 1 mg of TNF was coupled per mL of solid support matrix.

ASSEMBLY—The binding matrix (capture support 204) includes a single-chain TNF (SC-TNF) protein that is covalently linked to agarose beads. The device housing is comprised of a polycarbonate tube with two side ports for filling, capped with non-vented Luer caps. The end caps have male Luer ports and are tightly bound to the tube to create a fluidically sealed enclosure terminated at each end by the end cap Luer ports. Internal to the housing at the juncture between each end cap and the tube is a filter frit with an average pore size of 15-50 μm to retain the TNF ligand-coupled beads, the minimum diameter of which exceeds the pore size of the filter (e.g., as described above).

Example 2—Parameters for the Utilizing the Present System and Method

1. In configurations where pre- and post-column plasma concentration measurements are being taken to determine capture efficiency and/or leaching, which is not necessary for routine clinical applications, 3-way stopcock valves are attached to the inlet and outlet of the column end caps to enable periodic plasma sampling. 2. The system along with the attached stopcocks are connected into the plasma circuit of the apheresis machine. 3. The apheresis unit is configured with procedure-independent and/or procedure-specific operating parameters per the apheresis machine's instructions for use to complete steps 4, 6, and 10 below. 4. Flush the system with 1 L of normal saline prior to connecting the patient to the apheresis machine. 5. Connect the patient to the apheresis machine. 6. Treat the patient with the present system. 7. If applicable, collect blood and plasma samples in accordance with a study protocol and/or clinical treatment procedural plan. 8. Continuously monitor the patient's vital signs in accordance with typical apheresis treatment practice. 9. Continuously monitor the patient for adverse events before, during, and after the treatment. 10. Flush/rinse the device with normal saline post-treatment, re-cap the column with the retained end caps, and ensure proper storage and/or disposal of the used device.

The column of the present invention is intended to be used in conjunction with apheresis machines, such as the Terumo BCT or Spectra Optia System, for example, that are designed to accommodate plasma processing columns such as system 10. Such systems automate calculations based on the patient data and device parameters that are configured by the operator. In the event that the apheresis machine does not automate such calculations, the formulas identified in the tables below may be used.

TABLE 1

| Formula for Calculating Total Blood Volume | | | |
|---|---|---|---|
| Metric Units | Female | TBV = 183 + (356 × $H^3$) + (33.1 × W) | TBV = total blood volume (mL) |
| | Male | TBV = 604 + (367 × $H^3$) + (32.2 × W) | H = height (m) |
| | | | W = weight (kg) |
| English Units | Female | TBV = 183 + (0.005835 × $H^3$) + (15 × W) | TBV = total blood volume (mL) |
| | Male | TBV = 604 + (0.006012 × $H^3$) + (14.6 × W) | H = height (in) |
| | | | W = weight (lbs) |

TABLE 2

| Formula for Calculating Patient Plasma Volume | |
|---|---|
| Vp = 0.065 × W × (1 − HCT) | Vp = patient plasma volume (mL) |
| | W = weight (kg) |
| | HCT = hematocrit (%) |

TABLE 3

| Formula for Calculating Treatment Time | |
|---|---|
| T = (Vp × Vx)/Q | T = Treatment time (min) |
| | Vp = Patient plasma volume (mL) |
| | Vx = # of plasma volumes to be treated (unitless) |
| | Q = Flow rate (mL/min) |

INTENDED CLINICAL PERFORMANCE—The immunopheresis column of (e.g., system 10) is a device designed to successfully integrate with commercially available apheresis machines that use centrifugal or membrane separation techniques and that allow for secondary plasma processing (e.g., such as by system 10) to efficiently remove sTNF-Rs from the patient's plasma. The system disclosed herein meets the clinical performance requirements described below. Specified treatment times and flow rates have been verified to fall within the capabilities of modern apheresis systems using centrifugal separation techniques.

System Performance Specifications—1. Biological safety: Demonstrated to be biologically safe for use as an extracorporeal device supporting prolonged exposure to circulating blood. 2. Binding target: sTNF-Rs (includes sTNF-R1 and sTNF-R2). 3. Binding efficiency: >80% following 30 minutes of treatment at clinically-relevant flow rates. 4. Binding capacity: >230 μg of sTNF-Rs. 5. Flow rate (plasma): 60 mL/min. 6. Treatment time: approximately 2 hours. 7. Target plasma exchange volumes: 2 plasma volumes. 8. Leaching rate (TNFα): <50 ng/min. 9. Shelf life: >6 months @ 2-8° C. 10. Pressure tolerance: 776 mmHg.

Example 3—Efficacy of System 10 Based on In Vitro Parameters

PRECLINICAL TESTING—In vitro testing demonstrated that system 10 meets the performance and safety specifications defined in "Intended Clinical Performance" (previous section). The TNF-coupled binding matrix effectively captured over 98% of the sTNF-Rs in both spiked buffer solution and human plasma in the standard in vitro test, while maintaining a calculated sc-TNFα leaching rate of <50 ng/min (equivalent to a maximum of 6 μg in 2 hours), which is well below acceptable safety limits since the maximum tolerated dose (MTD) per day of TNFα is approximately 200 μg (see, for example, Goossens, V., et al. (1995) Proc. Natl Acad. Sci. USA, 92, 8115-8119). These performance and safety measures were replicated after beads were sterilized by E-Beam irradiation (15-30 kGy). Additionally, in this example, system 10 is designed for sustained flow rates of <300 mL/min, between 10 and 44 mL/min, and/or at 45 to 100 mL/min. The housing (e.g., 16 shown in FIG. 2 and FIG. 3) can withstand internal pressures of >776 mmHg, which is well above the typical back-pressure shut-off thresholds for commonly used apheresis machines.

Characterization of Binding Matrix (e.g., capture support 204)—Identity, purity, and integrity of the TNF ligand—A recombinant single chain TNFα ligand (sc-TNFα ligand, comprising 3 TNFα monomers) was used as a binding agent to capture sTNF-Rs. The TNFα has been characterized by assessing purity by high performance liquid chromatography (HPLC), integrity and identity by mass spectrometry, and functional strength by a flow test binding assay. HPLC was performed using a column with a phosphate buffer as the mobile phase at a flow rate of 1 mL/min. The integrity was measured by mass spectroscopy, which confirmed the calculated molecular weight of ~54 kD.

Binding efficiency of the binding matrix in sTNF-R spiked buffer—For the standard flow test, the amount of 2 mL of bead bed was obtained from an irradiated column of the present invention and transferred to a small column and tested for capture efficiency from phosphate buffer spiked with sTNF-R1 or sTNF-R2. TNF-R1 spiked buffer (20 ng/mL) was passed through the column at 10 ml/min, 5 mL/min, 2.5 mL/min, 5 mL/min and 10 mL/min, respectively. Samples were collected at 0.5 min intervals and assayed for sTNF-Rs. The result was greater than 98% capture efficiency for all the samples. Assaying for TNFα showed its release to be less than 7 ng/min.

Capture capacity of the binding matrix in sTNF-R spiked human plasma—To test the capacity of system 10, a column of the present invention was tested by running 1.8 liters of spiked human plasma through the device at flow rate of 45 mL/min. The human plasma used for each run was spiked with high concentrations of each receptor (9.74 ng/mL for sTNF-R1 and 127.5 ng/mL sTNF-R2). Samples of the post-column plasma were collected every 10 minutes and analyzed for sTNF-R concentration using a commercially-available, high-precision sTNF-R1/sTNF-R2 diagnostics kit. The amount of sTNF-R retained on the column was calculated to verify the capture efficiency and overall capacity.

Binding efficiency at each time point was calculated by comparing the pre- and post-column concentrations of sTNF-R. The binding matrix captured greater than 85% of sTNF-R1 and sTNF-R2. The binding efficiency was greater than 95% for sTNF-R1 throughout and although a lesser efficiency was observed for sTNF-R2, its capture still remaining at greater than 85%. The slight linear decrease in binding efficiency for sTNF-R2 is possibly attributed to the lower binding affinity of this soluble receptor for the TNFα ligand used.

The total amount of sTNF-R captured on the columns was determined by comparing pre- and post-treatment concentrations of sTNF-Rs. The column captured 230 μg of sTNF-R in the 15 mL/min run and 149.4 μg in the 45 mL/min run. Both of these values are in excess of the amount of approximately 30 μg of sTNF-Rs that is typically present in a cancer patient. The amount of total TNF-R capture for the 15 ml/min run at 80 minutes, the point where the column efficiency began to decrease, was 99.9 μg, which is still well in excess of the typical amount present in a cancer patient.

Leaching rate of TNFα from the device of the present invention—System 10 is configured to prevent the unintentional release (i.e., 'leaching') of TNFα from system 10 during its use to avoid infusing potentially pharmacologically-significant amounts into the patient. The TNF release from the beads was determined during conduct of a flow test. Phosphate buffered saline was spiked with approximately 20 ng/mL of sTNF-R1 and run through a 2 mL bead bed obtained from a system 10 (FIG. 1-3) column. The flow rate was sequentially performed at 10 mL/min, 5 mL/min, 2.5 ml/min, 5 mL/min and 10 mL/min for 30 seconds at each flow rate. Samples were analyzed according to a commercially-available, high-precision TNF diagnostics kit. The TNF leaching rate in ng/min was calculated by multiplying the concentration of TNF in the sample (ng/mL) by the flow rate (mL/min). The amount of release in the final fraction collected at 10 mL/min was 0.65 ng/min per 2 mL of beads or 0.325 ng/min/mL (0.65 ng/min/2 mL). In this example, the upper limit of the bead bed volume that would be within the specification of 50 ng/min is (50 ng/min)/(0.325 ng/min/mL) or 154 mL of beads.

Device housing integrity—Testing was conducted on empty housings (e.g., 16) of the present invention to verify that the integrity of system 10 is maintained at increased internal pressures. A side port (e.g., 206, 208) of system 10 was attached to a compressor using tubing and a connector. The capped housing was submerged in a water bath, pressurized to 776 mmHg and observed for air bubble generation. No device failures (presence of bubbles leaking from the submerged device) were observed. This test pressure exceeds the maximum pressure of the Optia unit (500 mmHg).

Example 4—Demonstration of Efficacy in a Canine Model

The effect of extracorporeal removal of sTNF-Rs, with system 10, from canines with naturally occurring solid malignant tumor or melanoma (Stage 4) was assessed in a proof-of-concept comparative oncology study. The study used system 10 with a sc-TNFα peptide-bead matrix. System 10 was used in conjunction with the Terumo BCT Spectra Optia Apheresis System for secondary plasma processing through system 10. Dual lumen catheters were employed in most dogs for vascular access, and extracorporeal anticoagulation was achieved with acid-citrate dextrose anticoagulation (ACDA) solution and reversed with calcium gluconate infusion as recommended per the Spectra Optia user operating manual. A total of 20 canines were treated. Canine patients received between 12-24 apheresis treatments over the course of the 4-8 week treatment phase of the study. Over 300 immunopheresis treatments were performed during this study.

Device Performance—To verify the in vivo safety and performance of the device, TNF and sTNF-Rs were measured every 30 minutes during treatment in pre- and post-column plasma (taken from the inlet and outlet ports of the device, respectively); and systemic (from blood) TNF and sTNF-Rs were measured before each treatment, every 30 minutes during treatment, and every 30 minutes after treatment (for the 1.5 hours immediately following treatment).

During each treatment, analysis of pre- and post-column (system 10) plasma showed that sTNF-R was efficiently and consistently removed over the course of each individual treatment without a measurable increase in TNF levels in the blood. Analysis of pre- and post-treatment plasma generally showed nearly a 50% reduction in systemic sTNF-R levels.

Device Safety and Clinical Efficacy—To evaluate the clinical safety and efficacy of the device, measurements of safety, tolerability, and impact on tumor progression were made throughout the study.

During the course of over 300 administered immunopheresis treatments across a total of 20 canines, there were few serious adverse events reported, and none that were attributed to the specific apheresis procedure or as a result of treatment with system 10 or removal of sTNF-Rs. The tolerability to treatment is best illustrated when examining the canine patient QoL data. Changes in QoL were generally scored as 'neutral' for most scores throughout the active treatment phase of the study, which included between 12-24 treatments per patient. Although some scores worsened, most showed stable parameters or improvement throughout the entire course of treatment, which for the Stage 4 patient population in the study represents a favorable outcome.

Treatment with the device of the present invention had an overall beneficial effect on tumor progression. The majority of canines (12/17 evaluable cases) were scored as "stable disease" (SD) at some point during treatment (data not shown) and 7 of the 17 evaluable canines showed a favorable treatment-related effect at the end of the treatment phase, with one case showing complete regression (CR).

Conclusions—The overall condition of the canines generally improved while they were on study, with an observable stabilization or reduction in tumor burden and an improvement in quality of life. In addition, the absence of clinically-significant safety issues are consistent with the established relative safety of general apheresis procedures and is compelling, as it presents the potential to provide clinically-meaningful benefit without the typical and significant side effects associated with traditional chemotherapy and radiation. This canine companion animal study showed that extracorporeal removal of sTNF-Rs utilizing the Apheresis Immunoadsorption Affinity Column of the present invention containing a sc-TNF peptide-bead matrix could be therapeutically effective in canines with cancer and provided compelling clinical evidence that use of such a device could be employed in human subjects.

Example 5—Biocompatibility

System 10 has been evaluated for biological safety in accordance with the Food & Drug Administration (FDA) Biocompatibility Testing Matrix and International Standard ISO 10993-1 (2009). System 10 can be categorized as an External Communicating Device, Circulating blood, with prolonged contact duration. This is the same testing categorization utilized for multiple other commercially available extracorporeal immunosorbent columns.

Biocompatibility tests were performed in accordance with 21 CFR Part 58 (Good Laboratory Practice for Nonclinical Laboratory Studies). All tests were conducted on the sterilized, finished devices by a certified, independent testing organization. Based upon the tests performed, the devices conform to the recommendations and principles contained within the ISO 10993-1 (2012) consensus standard, "Biological evaluation of medical devices—Part 1: Evaluation and testing within a risk management process," and with the FDA's associated guidance document issued Jun. 16, 2016.

Example 6—Demonstration of Safety in Human Subjects

A first-in-man, compassionate use clinical study has been conducted to collect pilot safety and performance data of system 10. The device was used in combination with the Terumo BCT Spectra Optia System with secondary plasma processing through system 10 as was done in the companion canine comparative oncology study (described above). Dual lumen catheters were employed for vascular access, based on experience from the canine study, and extracorporeal anticoagulation (ACDA solution) and reversal (with calcium gluconate infusion) was similar to that employed in the canine study and as recommended per the Spectra Optia user operating manual.

Apheresis Procedure Performance—System 10 was successfully utilized with the Terumo BCT Spectra Optia's apheresis equipment. For each treatment conducted, system 10 was able to be appropriately integrated into the extracorporeal plasma circuit. No device-attributed obstructions in the secondary plasma processing circuit (e.g., the circuit coupled to system 10) were reported. The system circuit integrity was consistently maintained (e.g., no leaks/fluid losses were reported) and all treatments were able to be successfully completed. Based upon this collective data, the device of the present invention appears to be suitable for use with the Terumo BCT Spectra Optia.

Safety and Tolerability Results—A total of 14 patients were enrolled in the study. All patients had advanced cancer for which current treatments had failed but were otherwise stable (baseline Eastern Cooperative Oncology Group (ECOG) score 0-2). The range of treatments each patient received varied (e.g., one patient received up to 16 treatments). A total of 93 individual treatments were completed with no unanticipated apheresis-related adverse events (AE) or adverse device effects (ADE) being reported. Based on the data collected from this study, Immunopheresis using the present approach and system 10 appears generally safe and well-tolerated.

Figure 11:
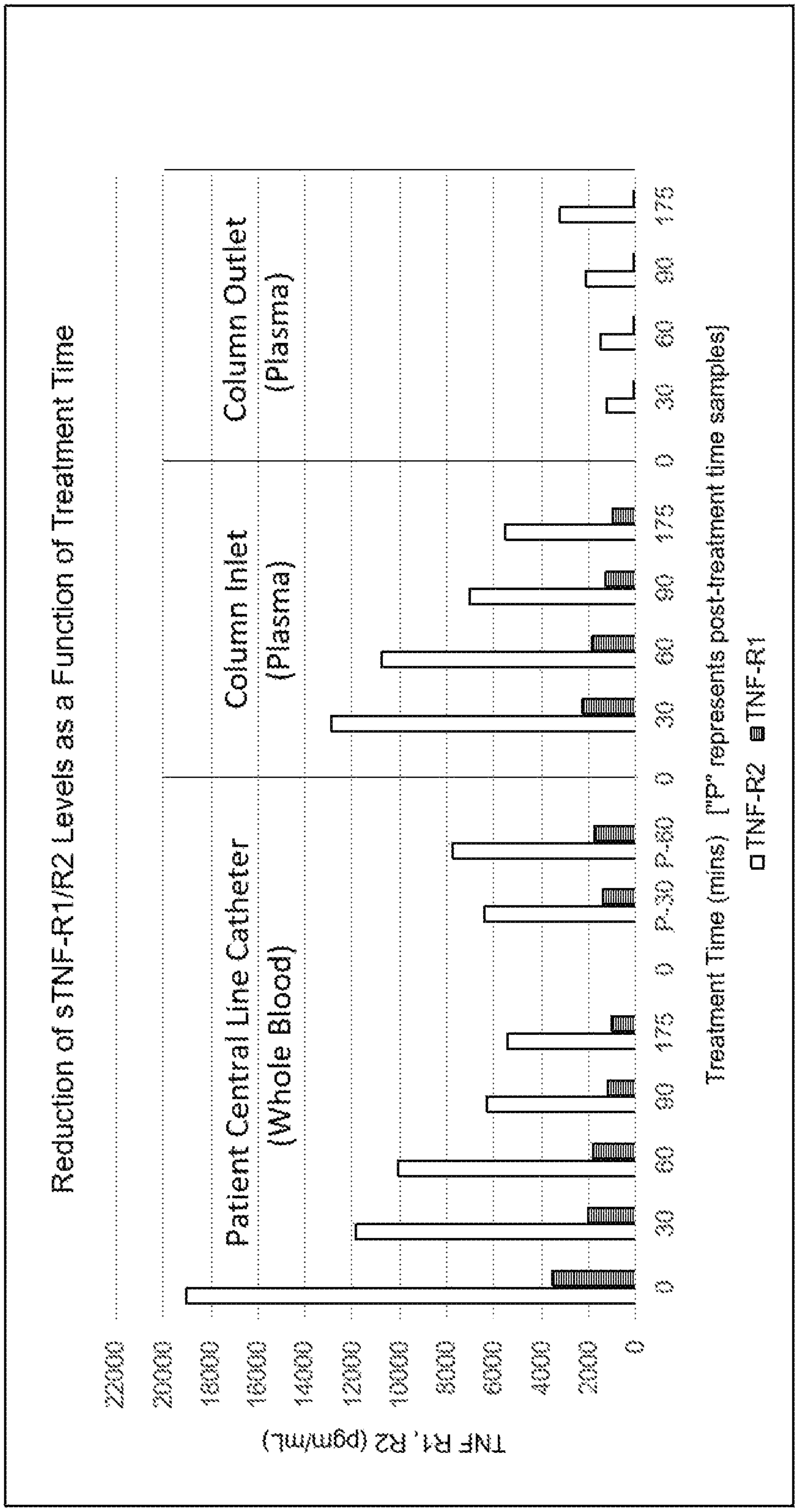
FIG. 11 illustrates representative system performance characteristics including sTNF-R1 and sTNF-R2 reduction from a patient's blood pool and column capture efficiency as a function of procedure time, in accordance with one or more embodiments.

FIG. 11 illustrates representative system 10 (FIG. 1-3) performance characteristics including sTNF-R1 and sTNF-R2 reduction from a human patient's blood pool and column capture efficiency as a function of procedure time. FIG. 11 is illustrative of typical system 10 performance results from a single human patient treatment. Samples of whole blood and plasma where drawn at baseline (T=0 mins), 30 mins., 60 mins., 90 mins., and at the end of treatment (i.e., completion of 2 plasma volumes circulated through the system), which in this example occurred 175 minutes from the procedure start time. At each time point, whole blood was drawn from the patient's central line catheter and plasma samples were taken at the inlet (e.g., 200 shown in FIG. 2-3) and outlet (e.g., 210 shown in FIG. 2-3) of system 10. Additionally, whole blood samples were drawn 30- and 60-minutes post-treatment. sTNF-R1 and sTNF-R2 concentrations in the samples were analyzed using a commercially-available, high-precision diagnostics assay. FIG. 11 shows a significant differential between corresponding inlet 200 and outlet 210 sTNF-R1 and sTNF-R2 concentrations at each time point demonstrating that system 10 was effectively capturing sTNF-R1 and sTNF-R2 throughout the course of treatment. Moreover, the steady time-based reduction in sTNF-R1 and sTNF-R2 concentrations observed in the patient's overall circulatory system (i.e. central line whole blood measurements) followed by rebounding levels 30- and 60-minutes post-treatment, indicates the therapeutic objective of reducing endogenous levels of sTNF-R1 and sTNF-R2 during the treatment period was effectively being accomplished.

What is claimed is:

1. A system for removing a target component from a body fluid of a patient, the system comprising:

a housing;

an inlet coupled to the housing and configured to receive the body fluid from the patient;

a sequestering chamber disposed within the housing and configured to receive the body fluid from the inlet;

a capture support disposed within the sequestering chamber and configured to bind to the target component;

an access port coupled to the housing and configured to facilitate insertion and/or removal of capture support to or from the sequestering chamber;

an outlet coupled to the housing and configured to pass the body fluid from the sequestering chamber for reintroduction of some or all of the body fluid back into the patient; and a filter housed within the housing and configured to separate the capture support in the sequestering chamber from the inlet and the outlet.

2. The system of claim 1, wherein a capture efficiency of the capture support binding to the target component is at least 80%.

3. The system of claim 2, wherein the capture efficiency is provided at a flow rate of 45 ml/min of the body fluid.

4. The system of claim 1, wherein a binding affinity of the capture support to the target component is greater than $10^{-7}$ KD.

5. The system of claim 1, wherein a leach rate of the capture support through the outlet is less than about 100 ng/ml/min.

6. The system of claim 1, further comprising an elution reagent port configured to facilitate introduction of an elution reagent into the sequestering chamber.

7. The system of claim 1, wherein the target component comprises a tumor necrosis factor (TNF) receptor.

8. The system of claim 1, wherein the capture support comprises a fragment of TNF.

9. The system of claim 1, wherein the capture support comprises TNFα, multimers of TNFα, single chain TNFα, fragments of TNFα, multimers of fragments of TNFα, or combinations thereof.

10. The system of claim 1, wherein the capture support comprises ligands bound to beads, and wherein the ligands have a given density and orientation on a given bead, the density and orientation configured to enhance binding between the ligands and the target component of the body fluid.

11. The system of claim 10, wherein a size, number, density, and/or concentration of the beads is configured to facilitate a laminar flow of the body fluid through the beads to enhance the binding between the ligands and the at least one target component of the body fluid.

12. The system of claim 10, wherein the beads are quenched in ethanolamine to enhance binding specificity.

13. The system of claim 1, further comprising a target component outlet port coupled to the housing configured to facilitate sampling or removal of all or part of captured target component without compromising the housing.

14. The system of claim 1, further comprising an elution reagent port coupled to the housing configured to facilitate introduction of an elution reagent into the sequestering chamber without compromising the housing.

* * * * *

SEQUENCE LISTING

<160> NUMBER OF SEQ ID NOS: 3

<210> SEQ ID NO 1
<211> LENGTH: 155
<212> TYPE: PRT
<213> ORGANISM: Homo sapiens

<400> SEQUENCE: 1

```
Ser Ser Ser Arg Thr Pro Ser Asp Lys Pro Val Ala His Val Val Ala
1               5                   10                  15

Asn Pro Gln Ala Glu Gly Gln Leu Gln Trp Leu Asn Arg Arg Ala Asn
            20                  25                  30

Ala Leu Leu Ala Asn Gly Val Glu Leu Arg Asp Asn Gln Leu Val Val
        35                  40                  45

Pro Ser Glu Gly Leu Tyr Leu Ile Tyr Ser Gln Val Leu Phe Lys Gly
    50                  55                  60

Gln Gly Cys Pro Ser Thr His Val Leu Leu Thr His Thr Ile Ser Arg
65                  70                  75                  80

Ile Ala Val Ser Tyr Gln Thr Lys Val Asn Leu Leu Ser Ala Ile Lys
                85                  90                  95

Ser Pro Cys Gln Arg Glu Thr Pro Glu Gly Ala Glu Ala Lys Pro Trp
            100                 105                 110

Tyr Glu Pro Ile Tyr Leu Gly Gly Val Phe Gln Leu Glu Lys Gly Asp
        115                 120                 125

Arg Leu Ser Ala Glu Ile Asn Arg Pro Asp Tyr Leu Asp Phe Ala Glu
    130                 135                 140

Ser Gly Gln Val Tyr Phe Gly Ile Ile Ala Leu
145                 150                 155
```

<210> SEQ ID NO 2
<211> LENGTH: 509
<212> TYPE: PRT
<213> ORGANISM: Artificial Sequence
<220> FEATURE:
<223> OTHER INFORMATION: Trimeric peptide

<400> SEQUENCE: 2

```
Met Cys Gly Ser His His His His His His Gly Ser Ala Ser Ser Ser
1               5                   10                  15

Ser Arg Thr Pro Ser Asp Lys Pro Val Ala His Val Val Ala Asn Pro
            20                  25                  30

Gln Ala Glu Gly Gln Leu Gln Trp Leu Asn Arg Arg Ala Asn Ala Leu
        35                  40                  45

Leu Ala Asn Gly Val Glu Leu Arg Asp Asn Gln Leu Val Val Pro Ser
    50                  55                  60

Glu Gly Leu Tyr Leu Ile Tyr Ser Gln Val Leu Phe Lys Gly Gln Gly
65                  70                  75                  80

Cys Pro Ser Thr His Val Leu Leu Thr His Thr Ile Ser Arg Ile Ala
                85                  90                  95

Val Ser Tyr Gln Thr Lys Val Asn Leu Leu Ser Ala Ile Lys Ser Pro
            100                 105                 110

Cys Gln Arg Glu Thr Pro Glu Gly Ala Glu Ala Lys Pro Trp Tyr Glu
        115                 120                 125

Pro Ile Tyr Leu Gly Gly Val Phe Gln Leu Glu Lys Gly Asp Arg Leu
    130                 135                 140

Ser Ala Glu Ile Asn Arg Pro Asp Tyr Leu Asp Phe Ala Glu Ser Gly
145                 150                 155                 160
```

Gln Val Tyr Phe Gly Ile Ile Ala Leu Gly Gly Gly Ser Gly Gly Gly
165 170 175

Ser Gly Gly Gly Ser Gly Gly Gly Ser Ser Ser Arg Thr Pro Ser Asp
180 185 190

Lys Pro Val Ala His Val Val Ala Asn Pro Gln Ala Glu Gly Gln Leu
195 200 205

Gln Trp Leu Asn Arg Arg Ala Asn Ala Leu Leu Ala Asn Gly Val Glu
210 215 220

Leu Arg Asp Asn Gln Leu Val Val Pro Ser Glu Gly Leu Tyr Leu Ile
225 230 235 240

Tyr Ser Gln Val Leu Phe Lys Gly Gln Gly Cys Pro Ser Thr His Val
245 250 255

Leu Leu Thr His Thr Ile Ser Arg Ile Ala Val Ser Tyr Gln Thr Lys
260 265 270

Val Asn Leu Leu Ser Ala Ile Lys Ser Pro Cys Gln Arg Glu Thr Pro
275 280 285

Glu Gly Ala Glu Ala Lys Pro Trp Tyr Glu Pro Ile Tyr Leu Gly Gly
290 295 300

Val Phe Gln Leu Glu Lys Gly Asp Arg Leu Ser Ala Glu Ile Asn Arg
305 310 315 320

Pro Asp Tyr Leu Asp Phe Ala Glu Ser Gly Gln Val Tyr Phe Gly Ile
325 330 335

Ile Ala Leu Gly Gly Gly Ser Gly Gly Gly Ser Gly Gly Gly Ser Gly
340 345 350

Gly Gly Ser Ser Ser Arg Thr Pro Ser Asp Lys Pro Val Ala His Val
355 360 365

Val Ala Asn Pro Gln Ala Glu Gly Gln Leu Gln Trp Leu Asn Arg Arg
370 375 380

Ala Asn Ala Leu Leu Ala Asn Gly Val Glu Leu Arg Asp Asn Gln Leu
385 390 395 400

Val Val Pro Ser Glu Gly Leu Tyr Leu Ile Tyr Ser Gln Val Leu Phe
405 410 415

Lys Gly Gln Gly Cys Pro Ser Thr His Val Leu Leu Thr His Thr Ile
420 425 430

Ser Arg Ile Ala Val Ser Tyr Gln Thr Lys Val Asn Leu Leu Ser Ala
435 440 445

Ile Lys Ser Pro Cys Gln Arg Glu Thr Pro Glu Gly Ala Glu Ala Lys
450 455 460

Pro Trp Tyr Glu Pro Ile Tyr Leu Gly Gly Val Phe Gln Leu Glu Lys
465 470 475 480

Gly Asp Arg Leu Ser Ala Glu Ile Asn Arg Pro Asp Tyr Leu Asp Phe
485 490 495

Ala Glu Ser Gly Gln Val Tyr Phe Gly Ile Ile Ala Leu
500 505

<210> SEQ ID NO 3
<211> LENGTH: 499
<212> TYPE: PRT
<213> ORGANISM: Artificial Sequence
<220> FEATURE:
<223> OTHER INFORMATION: Trimeric peptide

<400> SEQUENCE: 3

Gly Ser Ala Ser Ser Ser Ser Arg Thr Pro Ser Asp Lys Pro Val Ala
1 5 10 15

```
His Val Val Ala Asn Pro Gln Ala Glu Gly Gln Leu Gln Trp Leu Asn
            20                  25                  30

Arg Arg Ala Asn Ala Leu Leu Ala Asn Gly Val Glu Leu Arg Asp Asn
        35                  40                  45

Gln Leu Val Val Pro Ser Glu Gly Leu Tyr Leu Ile Tyr Ser Gln Val
    50                  55                  60

Leu Phe Lys Gly Gln Gly Cys Pro Ser Thr His Val Leu Leu Thr His
65                  70                  75                  80

Thr Ile Ser Arg Ile Ala Val Ser Tyr Gln Thr Lys Val Asn Leu Leu
                85                  90                  95

Ser Ala Ile Lys Ser Pro Cys Gln Arg Glu Thr Pro Glu Gly Ala Glu
            100                 105                 110

Ala Lys Pro Trp Tyr Glu Pro Ile Tyr Leu Gly Gly Val Phe Gln Leu
        115                 120                 125

Glu Lys Gly Asp Arg Leu Ser Ala Glu Ile Asn Arg Pro Asp Tyr Leu
    130                 135                 140

Asp Phe Ala Glu Ser Gly Gln Val Tyr Phe Gly Ile Ile Ala Leu Gly
145                 150                 155                 160

Gly Gly Ser Gly Gly Gly Ser Gly Gly Gly Ser Gly Gly Gly Ser Ser
                165                 170                 175

Ser Arg Thr Pro Ser Asp Lys Pro Val Ala His Val Val Ala Asn Pro
            180                 185                 190

Gln Ala Glu Gly Gln Leu Gln Trp Leu Asn Arg Arg Ala Asn Ala Leu
        195                 200                 205

Leu Ala Asn Gly Val Glu Leu Arg Asp Asn Gln Leu Val Val Pro Ser
    210                 215                 220

Glu Gly Leu Tyr Leu Ile Tyr Ser Gln Val Leu Phe Lys Gly Gln Gly
225                 230                 235                 240

Cys Pro Ser Thr His Val Leu Leu Thr His Thr Ile Ser Arg Ile Ala
                245                 250                 255

Val Ser Tyr Gln Thr Lys Val Asn Leu Leu Ser Ala Ile Lys Ser Pro
            260                 265                 270

Cys Gln Arg Glu Thr Pro Glu Gly Ala Glu Ala Lys Pro Trp Tyr Glu
        275                 280                 285

Pro Ile Tyr Leu Gly Gly Val Phe Gln Leu Glu Lys Gly Asp Arg Leu
    290                 295                 300

Ser Ala Glu Ile Asn Arg Pro Asp Tyr Leu Asp Phe Ala Glu Ser Gly
305                 310                 315                 320

Gln Val Tyr Phe Gly Ile Ile Ala Leu Gly Gly Gly Ser Gly Gly Gly
                325                 330                 335

Ser Gly Gly Gly Ser Gly Gly Gly Ser Ser Ser Arg Thr Pro Ser Asp
            340                 345                 350

Lys Pro Val Ala His Val Val Ala Asn Pro Gln Ala Glu Gly Gln Leu
        355                 360                 365

Gln Trp Leu Asn Arg Arg Ala Asn Ala Leu Leu Ala Asn Gly Val Glu
    370                 375                 380

Leu Arg Asp Asn Gln Leu Val Val Pro Ser Glu Gly Leu Tyr Leu Ile
385                 390                 395                 400

Tyr Ser Gln Val Leu Phe Lys Gly Gln Gly Cys Pro Ser Thr His Val
                405                 410                 415

Leu Leu Thr His Thr Ile Ser Arg Ile Ala Val Ser Tyr Gln Thr Lys
            420                 425                 430
```

-continued

```
Val Asn Leu Leu Ser Ala Ile Lys Ser Pro Cys Gln Arg Glu Thr Pro
        435                 440                 445

Glu Gly Ala Glu Ala Lys Pro Trp Tyr Glu Pro Ile Tyr Leu Gly Gly
    450                 455                 460

Val Phe Gln Leu Glu Lys Gly Asp Arg Leu Ser Ala Glu Ile Asn Arg
465                 470                 475                 480

Pro Asp Tyr Leu Asp Phe Ala Glu Ser Gly Gln Val Tyr Phe Gly Ile
                485                 490                 495

Ile Ala Leu
```